United States Patent
Dow et al.

(10) Patent No.: US 11,185,560 B2
(45) Date of Patent: Nov. 30, 2021

(54) ACTIVATED STEM CELLS AND SYSTEMIC TREATMENT METHODS FOR INFECTED WOUNDS

(71) Applicant: COLORADO STATE UNIVERSITY RESEARCH FOUNDATION, Fort Collins, CO (US)

(72) Inventors: Steven W. Dow, Littleton, CO (US); Lyndah Chow, Fort Collins, CO (US); Valerie Johnson, Fort Collins, CO (US)

(73) Assignee: COLORADO STATE UNIVERSITY RESEARCH FOUNDATION, Fort Collins, CO (US)

(*) Notice: Subject to any disclaimer, the term of this patent is extended or adjusted under 35 U.S.C. 154(b) by 181 days.

(21) Appl. No.: 15/781,972

(22) PCT Filed: Dec. 7, 2016

(86) PCT No.: PCT/US2016/065392
§ 371 (c)(1),
(2) Date: Jun. 6, 2018

(87) PCT Pub. No.: WO2017/100328
PCT Pub. Date: Jun. 15, 2017

(65) Prior Publication Data
US 2018/0360885 A1 Dec. 20, 2018

Related U.S. Application Data

(60) Provisional application No. 62/264,077, filed on Dec. 7, 2015.

(51) Int. Cl.
| | | |
|---|---|---|
| A61K 35/28 | (2015.01) | |
| A61P 17/02 | (2006.01) | |
| A61P 31/04 | (2006.01) | |
| A61K 35/00 | (2006.01) | |
| A61K 35/12 | (2015.01) | |
| A61K 9/00 | (2006.01) | |

(52) U.S. Cl.
CPC .............. *A61K 35/28* (2013.01); *A61K 35/00* (2013.01); *A61K 35/12* (2013.01); *A61P 17/02* (2018.01); *A61P 31/04* (2018.01); *A61K 9/0019* (2013.01)

(58) Field of Classification Search
None
See application file for complete search history.

(56) References Cited

U.S. PATENT DOCUMENTS

| | | |
|---|---|---|
| 9,321,994 B1 | 4/2016 | Betancourt |
| 2014/0134140 A1 | 5/2014 | Arnold et al. |

FOREIGN PATENT DOCUMENTS

| | | |
|---|---|---|
| KR | 100 717 724 B1 | 5/2007 |
| WO | WO 2012/051210 A2 | 4/2012 |
| WO | 2016053758 A1 | 4/2016 |
| WO | WO 2017/173150 A1 | 10/2017 |

OTHER PUBLICATIONS

Xuan et al., J Leukoc Biol. Jan. 2015;97(1):61-69 (Year: 2015).*
Zahorec, et al., "Mesenchymal stem cells for chronic wounds therapy", Cell and Tissue Banking, vol. 16(1), Mar. 21, 2014, pp. 19-26.
Johnson, "Activated mesenchymal stem cells amplify antibiotic activity against chronic *Staphylococcus aureus* infection (P5056)"; The Journal of Immunology, Supplement 180.11, May 1, 2013.
Zhao, et al., "The Toll-like Receiptor 3 Ligand, Poly(I:C) Improves Immunosuppressive Function and Therapeutic Effect of Mesenchymal Stem Cells on Sepsis via Inhibiting MiR-143", Stem Cells, vol. 32, No. 2, Jan. 13, 2014, pp. 521-533.
Delarosa et al., "Modulation of Adult Mesenchymal Stem Cells Activity by Toll-Like Receptors: Implications on Therapeutic Potential", Mediators of Inflammation, vol. 2010, Jan. 1, 2010, pp. 1-9.
The International Search Report and the Written Opinion of the International Searching Authority, PCT/US2016/065392, dated May 15, 2017, pp. 1-22.

* cited by examiner

*Primary Examiner* — Daniel C Gamett
(74) *Attorney, Agent, or Firm* — Polsinelli PC

(57) ABSTRACT

Provided herein are compositions containing an infusion ready population of activated, allogeneic mesenchymal stem cells and one or more pharmaceutically acceptable carriers, diluents, or excipients. Also provided are methods of treating infected wounds in mammals by administering an effective amount of activated mesenchymal stem cells to the mammal.

30 Claims, 27 Drawing Sheets

Immunostaining for intracellular production of the antimicrobial peptide LL-37

Immunostaining with isotype control antibody

Pre-treatment paw wound    Paw wound after 2 infusions of activated canine MSC.

1st MSC injection  2nd MSC injection  3rd injection  2 Weeks after last injection (Pre-treatment; MDR Staph +)

(Week 3; MDR Staph +)

(Week 5, culture negative)

(Week 7, culture negative)

ACTIVATED STEM CELLS AND SYSTEMIC TREATMENT METHODS FOR INFECTED WOUNDS

RELATED APPLICATIONS

This application is a national phase filing under 35 USC § 371 of International PCT Application for PCT/US2016/065392, filed on Dec. 7, 2016, which claims priority U.S. Application No. 62/264,077, filed on Dec. 7, 2015, the contents of which are herein incorporated by reference in its entirety.

FIELD OF THE INVENTION

The present invention related generally to the use of activated mesenchymal stem cells for the treatment of infected wounds.

BACKGROUND OF THE INVENTION

Wound healing is a complex, dynamic, and well-orchestrated process that is activated whenever disruption of the skin tissue occurs. A wide spectrum of events takes place through the wound-healing process. Wound infection is the most common and serious complication of tissue injuries such as traumatic and surgical wounds, chronic wounds and ulcers, and burns.

However, due to an increase globally in antibiotic resistance, there remains a critical unmet need in the art for additional, unconventional therapies for the treatment of wound infections.

SUMMARY OF THE INVENTION

Provided herein are compositions containing an infusion ready population of allogeneic mesenchymal stem cells that have been activated by exposure to one or more activating agents selected from a Toll-like receptor 3 (TLR3) agonist, a Toll-like receptor 9 (TLR9) agonist, a Toll-like receptor 4 (TLR4) agonist, r a nuclear oligodimerization domain (NOD) receptor agonist, an RIG-I receptor (RLR) agonist, a cytosolic DNA sensor (CDS) agonist, and/or a STING receptor agonist, and one or more pharmaceutically acceptable carriers, diluents, or excipients. For example, the composition may be formulated for intravenous administration.

Mesenchymal stem cells can be obtained or derived from any source known in the art, for example bone marrow, adipose tissue, cord blood, tissue biopsies (e.g., skin biopsies or dental biopsies), or induced pluripotent stem cells (iPSC).

In some embodiments, the population of allogeneic mesenchymal stem cells is activated by in vitro and/or ex vivo incubation with the one or more activating agents for at least 2 hours.

Non-limiting examples of suitable TLR3 agonists include polyadenylic-polyuridylic acid (poly(A:U), polyinosine-polycytidylic acid (pIC), and/or UV-inactivated viral particles (e.g., poxvirus particles).

Non-limiting examples of suitable TLR9 agonists include CpG oligodeoxynucleotides (CpG ODNs), inhibitory oligodeoxynucleotides (ODNs), purified DNA, and/or purified or synthetic plasmid DNA.

Non-limiting examples of TLR4 agonists include bacterial lipopolysaccharides (LPS), monophosphoryl lipid A (MPLA), and/or heat killed Gram-negative bacteria.

Non-limiting examples of NOD receptor agonists include NOD1 agonists (e.g., the dipeptide IE-DAP (iE-DAP (γ-D-Glu-mDAP)), NOD2 agonists (e.g., muramyldipeptide (MDP) and/or synthetic derivatives thereof such as mirabutide), and/or NOD1/2 mixed agonists (e.g., Gram positive bacteria and/or the synthetic molecule MurNAc-L-Ala-gamma-D-Glu-mDAP (a PGN-like molecule).

In some embodiments, the RLR receptor agonist is double stranded RNA, synthetic pAT RNA, and/or synthetic pIC RNA; the CDS agonist is double stranded DNA isolated from bacteria; and/or the STING receptor agonist is a cyclic dinucleotide, including, but not limited to 3,3 cyclic gAMP, 2,3 cyclic gAMP, 2,2 cyclic gAMP, and cyclic Di-GMP and/or cyclic di-UMP.

In one embodiment, the activating agent is 10 μg/ml poly inosinic:polycytidylic acid (pIC).

Any of the combinations described herein, may further include an effective amount of one or more antimicrobial agents such as a bactericidal antibiotic and/or a bacteriostatic antibiotic. Non-limiting examples of suitable bactericidal antibiotics may include penicillin derivatives (penams), cephalosporins (cephams), monobactams, carbapenems, vancomycin, daptomycin, fluoroquinolones, metronidazole, nitrofurantoin, co-trimoxazole, telithromycin, and/or aminoglycosidic antibiotics. Non-limiting examples of bacteriostatic antibiotics may include tetracycline antibiotics, choloramphenicol, erythromycin, clindamycin, and/or linezolid.

Additionally, in some embodiments, the activated mesenchymal stem cells can be preloaded with one or more antibiotics prior to administration.

Suitable allogenic mesenchymal stem cells are mammalian mesenchymal stem cells include human mesenchymal stem cells.

The compositions described herein enhance healing of a chronically-infected wound with MDR bacteria in a mammal.

Also provided are methods of treating a chronically infected wound in a mammal by administering an effective amount (e.g., 2×10$^6$ cells per kg body weight of the mammal) of activated mesenchymal stem cells to the mammal. For example, the cells can be administered by intravenous catheter over a period of 15 minutes.

Those skilled in the art will recognize that an effective amount of any of the compositions described herein can also be used in methods of treating a chronically infected wound in a mammal. In such methods, the activated mesenchymal stem cells or compositions induce bacterial clearance, reduce bacterial burden, or induce bacterial clearance and reduce bacterial burden in the infected wound.

Preferably, the activated mesenchymal stem cells are administered systemically (i.e., intravenously) to the mammal.

In any of the methods described herein, the mesenchymal stem cells are activated in vitro or ex vivo by incubation with one or more activating agents selected from a Toll-like receptor 3 (TLR3) agonist, a Toll-like receptor 9 (TLR9) agonist, a Toll-like receptor 4 (TLR4) agonist, a nuclear oligodimerization domain (NOD) receptor agonist, an RIG-I receptor (RLR) agonist, a cytosolic DNA sensor (CDS) agonist, and/or a STING receptor agonist.

Non-limiting examples of suitable TLR3 agonists include polyadenylic-polyuridylic acid (poly(A:U), polyinosine-polycytidylic acid (pIC), and/or UV-inactivated viral particles (e.g., poxvirus particles).

Non-limiting examples of suitable TLR9 agonists include CpG oligodeoxynucleotides (CpG ODNs), inhibitory oligodeoxynucleotides (ODNs), purified DNA, and/or purified or synthetic plasmid DNA.

Non-limiting examples of TLR4 agonists include bacterial lipopolysaccharides (LPS), monophosphoryl lipid A (MPLA), and/or heat killed Gram-negative bacteria.

Non-limiting examples of NOD receptor agonists include NOD1 agonists (e.g., the dipeptide IE-DAP (iE-DAP (γ-D-Glu-mDAP)), NOD2 agonists (e.g., muramyldipeptide (MDP) and/or synthetic derivatives thereof such as mirabutide), and/or NOD1/2 mixed agonists (e.g., Gram positive bacteria and/or the synthetic molecule MurNAc-L-Ala-gamma-D-Glu-mDAP (a PGN-like molecule).

In some embodiments, the RLR receptor agonist is double stranded RNA, synthetic pAT RNA, and/or synthetic pIC RNA; the CDS agonist is double stranded DNA isolated from bacteria; and/or the STING receptor agonist is a cyclic dinucleotide, including, but not limited to 3,3 cyclic gAMP, 2,3 cyclic gAMP, 2,2 cyclic gAMP, and cyclic Di-GMP and/or cyclic di-UMP.

In one embodiment, the mesenchymal stem cells are activated with poly inosinic:polycytidylic acid (pIC) prior to administration. For example, the mesenchymal stem cells are activated by incubation with poly inosinic:polycytidylic acid (pIC) in vitro at 10 μg/ml for at least 2 hours.

Any of the methods described herein may additional involve the administration of an effective amount of one or more antimicrobial agents, such as a bactericidal antibiotic (e.g., penicillin derivatives (penams), cephalosporins (cephams), monobactams, carbapenems, vancomycin, daptomycin, fluoroquinolones, metronidazole, nitrofurantoin, co-trimoxazole, telithromycin, and/or aminoglycosidic antibiotics) and/or a bacteriostatic antibiotic (e.g., tetracycline antibiotics, choloramphenicol, erythromycin, clindamycin, and/or linezolid).

The mesenchymal stem cells are mammalian mesenchymal stem cells (e.g., allogeneic mesenchymal stem cells and/or human mesenchymal stem cells).

In any of the methods described herein, the activated mesenchymal stem cells or compositions thereof enhance healing of an infected wound in the mammal. By way of non-limiting example, the infected wound is selected from abrasions, lacerations, contusions, concussions, stab wounds, skin cuts, surgical wounds, gunshot wounds, burns, sunburns, frostbite, chemical wounds, bites, stings and electrical wounds.

In various embodiments, the wounds may be chronic wounds infected with highly drug-resistant bacteria or chronic wounds that are infected by more than one (i.e., 2, 3, 4, 5, or more) strain or species of bacteria.

Additionally, any of the methods described herein can also be used to treat wounds in patients with type I or type II diabetes mellitus. Such patients are known to have immune defects that make treatment of chronic and/or infected wounds difficult.

The activated mesenchymal stem cells utilized in the methods and uses described herein have increased antimicrobial activity compared to mesenchymal stem cells that have not been activated.

In one preferred embodiment, the activated MSC are administered intravenously and are administered concurrently with antibiotic therapy, including either bactericidal or bacteriostatic antibiotics.

In any of the methods or uses described herein, the activated mesenchymal stem cells can be administered at the time of or after the wound occurs.

In another aspect, the invention provides activated mesenchymal stem cells for use in treating a chronically infected wound in a mammal. The activated mesenchymal stem cells are for administration in a therapeutically effective amount.

In a further aspect, the invention provides a composition of the invention for use in treating a chronically infected wound in a mammal. For example, the composition is for administration in a therapeutically effective amount.

Any of the features of the methods of treatment (e.g., features of the mesenchymal stem cells and/or the compositions described herein) are equally applicable to both the method of treatment and medical use aspects of the invention.

Any of the aspects and embodiments described herein can be combined with any other aspect or embodiment as disclosed here in the Summary of the Invention, in the Drawings, and/or in the Detailed Description of the Invention, including the below specific, non-limiting, examples/embodiments of the present invention.

Unless otherwise defined, all technical and scientific terms used herein have the same meaning as commonly understood by one of ordinary skill in the art to which this application belongs. In the specification, the singular forms also include the plural unless the context clearly dictates otherwise.

Although methods and materials similar to or equivalent to those described herein can be used in the practice and testing of the application, suitable methods and materials are described below. All publications, patent applications, patents, and other references mentioned herein are incorporated by reference.

The references cited herein are not admitted to be prior art to the claimed application. In the case of conflict, the present specification, including definitions, will control. In addition, the materials, methods, and examples are illustrative only and not intended to be limiting.

Other features and advantages of the application will become apparent from the following detailed description in conjunction with the examples.

DETAILED DESCRIPTION OF THE INVENTION

Figure 1:
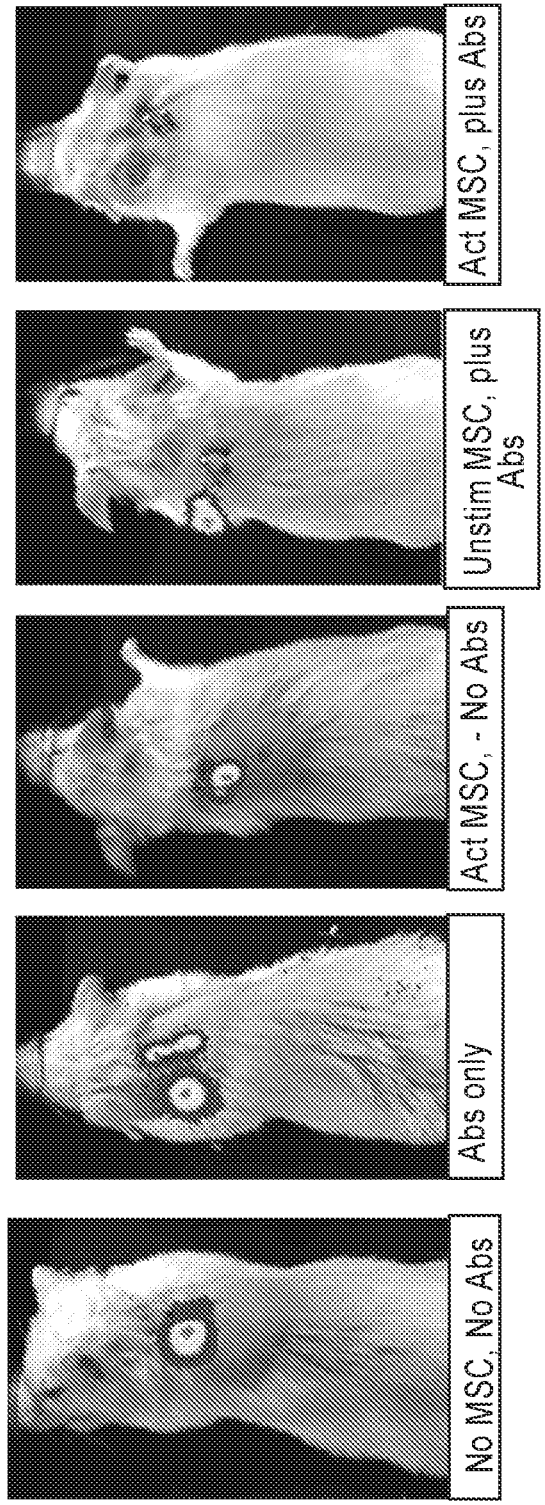
FIG. 1 is a series of photographs showing the effects of antimicrobial stem cell treatment in a mouse chronic *Staphylococcus aureus* wound infection model with biofilm formation. (See Walton et al., Comp Med. 64(1):25-33 (2014), which is herein incorporated by reference).

Chronic wound infections continue to be a major source of morbidity and mortality, driven in part by the increasing prevalence of drug-resistant bacteria and greater incidence of diseases such as diabetes mellitus that predispose to chronic wounds and wound infections. (See Owens et al., J. Hosp. Infect 70(Suppl. 2):3-10 (2008); Vinh et al., J. Long Term Eff. Med. Implants 15(5):467-88 (2005); Tuttle et al., Adv. Wound Care (New Rochelle) 4(1): 1-11 (2015); and Edmiston et al., Adv. Exp. Med. Biol. 830:47-67 (2015)). Infections characterized by the development of bacterial biofilms, which most often develop on the surface of implants such as catheters or orthopedic devices, are particularly difficult to manage with antibiotic therapy alone, often requiring weeks to months of continuous therapy. Despite aggressive antibiotic therapy, in many cases biofilm-infected devices or implants must be removed to fully resolve these chronic infections.

Provided herein are mesenchymal stem cells (MSC) that have been activated in vitro or ex vivo using specific immune activating compounds in order to increase their antimicrobial activity and their wound healing activity. Such activated MSC can be administered systemically using specific intravenous (i.v.) infusion techniques, either alone or in combination with one or more additional antibiotic therapies (i.e., one or more bactericidal and/or bacteriostatic antibiotics), to reach and treat chronic wound infections in sites that may be inaccessible to conventional direct injection (e.g., infections of orthopedic implants).

These activated MSCs (and any compositions thereof) can be used for the treatment of chronic, traumatic, and/or post-operative wound infections that often involve multi-drug resistant bacteria that form biofilms, making treatment particularly problematic. In embodiments, activated MSCs and compositions thereof will be useful for the treatment of highly antibiotic drug resistant infections and/or infections caused by multiple strains of the same or different antibiotics.

Moreover, activated MSCs can be used to treat wounds in patients (e.g., patients with diabetes mellitus) where the host immune status is often a contributory factor in the inability of antibiotic therapy alone to be fully effective and where defects in both innate and adaptive immunity are well recognized.

In any of the methods or uses described herein, antibiotics to which the wound infecting bacteria are resistant can still be co-administered with the activated MSC to achieve effective bacterial clearance, due in part to the ability of MSC to enhance the effectiveness of antibiotics. In fact, in any of the methods or uses described herein, it is essential that an antibiotic (even one to which the infecting bacterial are resistant) be co-administered with the activated MSC.

Systemically administered, activated MSCs interact with antibiotics and the host innate immune system to reduce bacterial burden and stimulate wound healing. Therefore, systemic activated MSC administration is a new non-antibiotic approach to enhance the efficacy of conventional antimicrobial therapy for chronic, deep-seated wound infections.

The net result of the interactions between MSC and antibiotic therapy is significant clearance of bacteria even from heavily infected synthetic implant materials such as mesh coated with *S. aureus* or *E. coli* or *Pseudomonas* or *Enterococcus* or any number of bacteria which form biofilms in vivo. Moreover, MSC administration also produced other benefits, including stimulation of wound healing and reduction of wound-associated inflammation and fibrosis.

Multiple complementary mechanisms of action likely account for the ability of activated MSC to help control wound infections. Thus, the net effect of MSC administration on bacterial burden likely reflects the sum of both direct and indirect mechanisms of action. One direct mechanism of antibacterial action demonstrated was secretion of antimicrobial peptides such as cathelicidins by MSC. Indirect mechanisms of bacterial elimination by MSC involved interactions of activated MSC with the host innate immune response.

Definitions

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

Unless specifically stated or obvious from context, as used herein, the terms "a," "an," and "the" are understood to be singular or plural.

Unless specifically stated or obvious from context, as used herein, the term "or" is understood to be inclusive.

As used herein, the term "about," unless indicated otherwise, refers to the recited value, e.g., amount, dose, temperature, time, percentage, etc., ±10%, ±9%, ±8%, ±7%, +6%, ±5%, ±4%, ±3%, ±2%, or ±1%.

The term "wound" refers to an injury to living tissue cause by a cut, blow, or other impact that may involve the laceration of a membrane (e.g., skin) and may result in damage to underlying tissues. Wounds include both open and closed wounds. Examples of "wounds" may include, but are not limited to non-penetrating wounds (e.g., abrasions, lacerations, contusions, concussions); penetrating wounds (e.g., stab wounds, skin cuts, gunshot wounds, traumatic wounds and fractures from automobile accidents or other traumas); thermal wounds (e.g., burns, sunburns, frostbite); chemical wounds (e.g., acids or alkalis); bites and stings (e.g., from humans, dogs, bats, rodents, snakes, scorpions, spiders, and/or ticks); and electrical wounds. Other important wound categories include post-operative wound infections, which may include infections of soft tissue surgery sites (e.g., tumor excision, cardiac surgery, organ transplants), infections of orthopedic implants (e.g., infected knee or hip prostheses), infections of implanted devices (e.g., infected pacemakers), and infections of chronic catheters (e.g., infection of PIC lines or indwelling urinary catheters).

An "infected wound" refers to any wound that has been infiltrated by microorganisms such as bacteria, along with an obvious host response (neutrophil and macrophage infiltration, granulation tissue, fibrosis).

Wounds may be chronic or acute. A "chronic wound" is a wound that does not heal in a predicable amount of time (i.e., within several weeks or months of the initial wound occurrence) and in an orderly set of stages. These wounds also typically harbor populations of bacteria that have formed bacterial biofilms, which can form on the surface of artificial implanted materials, but can also develop on host tissues (e.g., diabetic foot ulcers). The development of the bacterial biofilm state renders the bacteria much more refractory to treatment with antibiotics or other agents, particularly when the wounds are in sites inaccessible to topical treatment. In addition, chronic wounds are also much more likely to harbor multi-drug resistant bacteria due to a long prior history of treatment with antibiotics. Thus, chronic wounds are nearly always much more difficult to treat because of the co-evolution of bacterial resistance mechanisms and antibiotic selection pressure for drug resistance. These infections typically also involve one or more multi-drug resistant (MDR) strains of bacteria. Such bacteria include Gram-negative pathogens (e.g., *E. coli, Acinetobacter, Klebsiella, Enterobacter, Pseudomonas*) and Gram-positive pathogens (e.g., *Staphylococcus, Streptococcus, Enterococcus*). It should also be noted that virtually all strains of bacteria, both Gram negative and Gram-positive, are capable of forming biofilms in vivo. Chronic wounds may be the result of highly drug resistant bacterial infections and/or the result of infections with multiple strains or species of the same or different bacteria.

By way of non-limiting example, chronic infected wounds may include pressure ulcers, decubitus ulcers, arterial ulcers, venous ulcers, venous stasis ulcers, diabetic foot ulcers, traumatic ulcers, and/or burn ulcers, as well as implant infections (knee, ankle, hip prostheses), medical device infections (indwelling venous access or urinary tract catheters, pacemakers, defibrillators, stents for venous or arterial stenosis), mesh implants (e.g., vaginal and peritoneal slings, vascular filters) and orthopedic repair infections (e.g., infections of bone plates, screws, pins, and other fixation devices). Chronic wounds may also develop in diabetic patients, who are known to have immune defects that make wounds difficult to treat.

In contrast, an "acute wound" is an injury that develops rapidly (i.e., <1 week) and that heals without any complications in a predictable amount of time with a predictable antibiotic treatment regime.

As used herein, a "disorder" refers to any disorder, disease, or condition that would benefit from an agent that initiates, accelerates, promotes or enhances wound healing (including acute wounds, dehiscent wounds, and slow-healing delayed-healing and chronic wounds). Such wounds would include wounds in diabetic patients (e.g., foot ulcers or other cutaneous infections) or patients with reduced blood supply due to peripheral vascular disease (e.g., decubital ulcers, skin infections, limb infections). Thus, the agent would be expected to reduce inflammation, reduce or lessens scarring, improve scar quality, reduces fibrosis, and/or reduces adhesions. For example, diseases, disorders, and conditions include acute wounds, dehiscent wounds, as well as slow-healing delayed-healing and chronic wounds.

Importantly, the treatment would be expected to significantly shorten the duration of treatment necessary to induce resolution of infection, and to also reduce the numbers of treatments and the doses of antibiotics required.

Also included are diseases, disorders, and conditions characterized by excess production of fibrous material, including excess production of fibrous material within the extracellular matrix; diseases, disorders and conditions characterized by replacement of normal tissue elements by abnormal, non-functional, and/or excessive accumulation of matrix-associated components; diseases, disorders and conditions characterized by adhesion formation; and/or any disorder, disease, or condition that would benefit from an agent that promotes wound healing and/or reduces swelling, inflammation, and/or scar formation (including abnormal and excessive scarring, including keloid scars, hypertrophic scars, widespread (stretched) scars, and atrophic (depressed) scars). For example, included are wounds resulting from surgery or trauma, wounds that do not heal at expected rates (such as delayed-healing wounds, incompletely healing wounds, chronic wounds, and dehiscent wounds), and wounds associated abnormalities in connection with neuropathic, ischemic, microvascular pathology, pressure over bony area (tailbone (sacral), hip (trochanteric), buttocks (ischial), or heel or toes of the foot), reperfusion injury, and valve reflux etiology and conditions. Also included are diseases, disorders and conditions that would benefit from enhanced cellular migration, lessened cellular adhesion, scarring and inflammation as described herein.

As used herein, the terms "patient" or "subject" are used interchangeably herein to refer to any mammal, including humans, domestic and farm animals, and zoo, sports, and pet animals, such as dogs, horses, cats, and agricultural use animals including cattle, sheep, pigs, and goats. One preferred mammal is a human, including adults, children, and the elderly. Even more preferred humans would be those with type I or type II diabetes with chronic, non-healing infected wounds. A subject may also be a pet animal, including dogs, cats and horses. Preferred agricultural animals would be cattle and goats.

The terms "treat", "treating", "treatment" and the like, as used herein, unless otherwise indicated, refers to reversing, alleviating, inhibiting the process of, or preventing the disease, disorder or condition to which such term applies, or one or more symptoms of such disease, disorder or condition and includes the administration of any of the compositions, pharmaceutical compositions, or dosage forms described herein, to prevent the onset of the symptoms or the complications, or alleviating the symptoms or the complications, or eliminating the disease, condition, or disorder. Preferably, treatment is curative or ameliorating.

As used herein, "preventing" means preventing in whole or in part, or ameliorating or controlling, or reducing or halting the production or occurrence of the thing or event, for example, the disease, disorder or condition, to be prevented.

The phrases "therapeutically effective amount" and "effective amount" and the like, as used herein, indicate an amount necessary to administer to a patient, or to a cell, tissue, or organ of a patient, to achieve a therapeutic effect, such as an ameliorating or alternatively a curative effect. The effective amount is sufficient to elicit the biological or medical response of a cell, tissue, system, animal, or human that is being sought by a researcher, veterinarian, medical doctor, or clinician. Determination of the appropriate effective amount or therapeutically effective amount is within the routine level of skill in the art.

The terms "administering", "administer", "administration" and the like, as used herein, refer to any mode of transferring, delivering, introducing, or transporting a therapeutic agent to a subject in need of treatment with such an agent. Such modes include, but are not limited to, oral, topical, intravenous, intraperitoneal, intramuscular, intradermal, intranasal, and subcutaneous administration.

As used herein, the terms "bactericidal", "bactericidal antibiotics" and the like refer to antibiotics that kill bacteria, as opposed to "bacteriostatic antibiotics", which are antibiotics that slow the growth or reproduction of bacteria. Bactericidal antibiotics kill bacteria by inhibiting cell wall synthesis and/or by inhibiting bacterial enzymes or protein translation. Examples of bactericidal antibiotics include, but are not limited to, the beta-lactam antibiotics (e.g., penicillin derivatives (penicillins and semi-synthetic penicillins, with or without beta-lactamase inhibitors such as clavulanic acid), cephalosporins (cephamns), monobactams, and carbapenems) and vancomycin, daptomycin, fluoroquinolones, metronidazole, nitrofurantoin, co-trimoxazole, telithromycin, and aminoglycoside antibiotics. However, it should also be noted that treatment with activated MSC may also improve bacterial clearance by bacteriostatic antibiotics, including chloramphenicol and tetracyclines. Multiple classes of antibiotics (i.e., one or more bactericidal antibiotics alone or in combination with one or more bacteriostatic antibiotics) may be used.

"Toll-like receptors (TLRs)" refer to a class of proteins that play a key role in the innate immune system. These proteins are typically expressed in sentinel cells of the immune system such as macrophages and dendritic cells. They recognize structurally conserved molecules derived from microbes. Examples of TLRs include TLR1, TLR2, TLR3, TLR4, TLR5, TLR6, TLR7, TLR8, TLR9, TLR10, TLR11, TLR12, and TLR13. Most preferred would be TLRs known to be expressed by MSC, including TLR2, TLR3, TLR4, TLR7/8 and/or TLR9.

"Nucleotide-binding oligomerization domain (NOD) receptors" also play a key role in regulation of innate immune response. They are found in lymphocytes, macrophages, dendritic cells, and nonimmune cells (i.e., in epithelium and MSC) and can cooperate with TLRs or act alone to regulate inflammatory responses.

Other classes of innate immune receptors, including RIG-1 or STING or CDA receptors also play a key role in activating innate immune responses following intracellular introduction of stimulatory ligands, especially viral and bacterial nucleic acids. They are found in lymphocytes, macrophages, dendritic cells, and nonimmune cells (i.e., in epithelium and MSC) and can cooperate with TLRs or act alone to regulate inflammatory responses.

As used herein, the term "agonist" refers to a substance that initiates a physiological response when combined with a receptor. In contrast, an "antagonist" is a substance that interferes with or inhibits the physiological action of another.

Wound Healing

Wound healing, the process by which a body tissue (i.e., skin) repairs itself following trauma or injury, is typically divided into several phases: hemostasis (blood clotting), inflammation, proliferation (tissue growth), and maturation (tissue remodeling).

Skin tissue injury and disruption of blood vessels is followed by the formation of the fibrin clot, which functions to slow or prevent further bleeding and provides the substrate for cell migration into the wound. This is the hemostasis stage of wound healing.

Next, during the inflammation stage, neutrophils, which are attracted by a range of molecules, phagocytose foreign bodies and bacteria and are rapidly joined by monocytes that differentiate to macrophages. Macrophages, in turn, phagocytose microorganisms, fragments of the extracellular matrix, fibrin, neutrophils, erythrocytes, and other debris and also secrete a variety of molecules that are considered crucial for effective wound repair. In chronic wounds, one or more of the components of this phase may be dysregulated, thereby leading to delayed wound healing. Macrophages of the M2 phenotype are considered the most effective in stimulating wound healing.

During the proliferation stage, angiogenesis, collagen deposition, fibroplasia and granulation tissue formation, epithelialization, and wound contraction occur. Finally, during the maturation and remodeling phase, collagen is realigned, the tensile strength of the wound increases, and any unnecessary cells are removed by apoptosis.

While these phases of wound healing normally progress in a predictable manner, when they do not, a chronic wound or pathological scarring may result. The rate, speed, and/or efficacy at which wound healing progresses can be influenced by local and/or systemic factors. For example, local factors may include moisture, mechanical factors, edema, ischemia and necrosis, presence of foreign bodies, low oxygen tension, and/or perfusion. Systemic factors may include inflammation, diabetes, nutrient status, metabolic diseases, immunosuppression, connective tissue disorders, smoking, age, and/or alcohol consumption.

Complications of wound healing may include the development of chronic infection, deficient or excessive scar formation, exuberant granulation, and/or deficient wound contraction. Of these complications, the most serious is the development of chronic infections, particularly infections associated with biofilm formation, including infections of cutaneous and bony tissues, infections of orthopedic or surgical implants, or infections of materials used for surgical repair, including metallic orthopedic material (plates, screws, pins), meshes (vascular filters, reconstructive meshes), and medical implants (pacemakers, shunts) and vascular access ports and catheters. These infections typically also involve multi-drug (MDR) resistant strains of bacteria. Such bacteria include Gram-negative pathogens (e.g., *E. coli, Acinetobacter, Klebsiella, Enterobacter, Pseudomonas*) and Gram-positive pathogens (e.g., *Staphylococcus, Streptococcus, Enterococcus*). It should also be noted that virtually all strains of bacteria, both Gram negative and Gram-positive, are capable of forming biofilms in vivo.

Mesenchymal Stem Cells Mesenchymal stem cells (MSC) are multipotent stem cells that are capable of differentiating into osteoblasts, chondrocytes, myocytes, and adipocytes. Under tissue culture conditions, MSC exhibit plastic adherent properties and are most often classified as $CD73^+$, $CD90^+$, $CD105^+$, $CD11b^+$, $CD14^-$, $CD19^-$, $CD34^-$, $CD45^-$, $CD79a^-$, and $HLA-DR^-$ cells, though it should be noted that MSC isolated from different tissue sources will display different surface phenotypes. The antimicrobial properties of MSC may vary from one tissue source to another, and are therefore considered somewhat unpredictable in terms of their effectiveness for combatting bacterial infection.

Mesenchymal stem cells (MSC) are a subpopulation of cells of neural crest origin that exist in most tissues in the body in low numbers. Mesenchymal stem cells from a variety of sources have been shown to have antimicrobial activity in sepsis, wound healing, and infections in animal models. (See Krasnodembskaya, et al., Stem Cells 28(12): 2229-38 (2010); Krasnodembskaya, et al., Am J Physiol Lung Cell Mol Physiol 302(10):L1003-13 (2012); Al-Anazi et al., "Chapter 9: Mesenchymal Stem Cells—Their Antimicrobial Effects and Their Promising Future Role as Novel Therapies of Infectious Complications in High Risk Patients", dx.doi.org/10.5772/60640 (2015); Maxson, et al., Stem Cells Trans Med 1(2): 142-49 (2012); and Mei, et al., Am J Respir Crit Care Med 182(8): 1047-57 (2010). The presence of Toll-like receptors (TLRs) on MSCs and the impact of TLR ligands on MSC activity has also been studied. (See Lieneke I. Bouwman, Thesis entitled, "Microbial ligands alter the fate of stem cells—TLR activation influences survival, proliferation, differentiation, and function of stem cells", Universiteit Utrecht, Faculty of Veterinary Medicine, department Infectious Diseases & Immunology, Jul. 13, 2009). The results of these studies has been a wealth of often contradictory information regarding the effects of MSC on the properties that ultimately are result. For example, researchers have shown that activation of MSCs with a ligand of TLR3 actually increases the immunosuppressive function of MSCs, an effect that would normally be contraindicated for treatment of wounds. (See Zhou et al., Nat Commun 5:3619 (2014); Cassatella, et al., Stem Cells 29(6): 1001-11 (2011); and Zhao et al., Stem Cells 32(2): p. 521-33 (2014). Thus, the net effects (positive or negative) that result from pre-activation of MSCs through their TLRs are very difficult to predict, particularly when it comes to treatment of chronically infected wounds, which exhibit a complex interaction between bacteria and bacterial biofilms, and the immune response that develops over time.

However, the use of MSCs (or compositions thereof) to treat chronic biofilm infections has not previously been evaluated.

MSCs can be obtained or derived from a variety of tissues including, for example, bone marrow, adipose tissue, placenta, amniotic fluid, umbilical cord tissue, umbilical cord blood, adult muscle, corneal stroma, skin tissue, and/or dental pulp.

Most experimental and clinical studies with MSC use cells derived from bone marrow (BM-MSC) or from adipose tissues (Ad-MSC). However, the use of BM-MSC and Ad-MSC does potentially involve drawbacks because, when autologous MSC are used, the age of the donor greatly affects the immunological and antimicrobial properties of the MSC, as cells from older patients or animals typically are less functional. Moreover, when MSC from unrelated donors (i.e., allogeneic MSC) are used, there are issues with donor-to-donor variability and assurance of pathogen-free MSC. In addition, MSC can undergo only limited expansion in vitro before they undergo senescence and lose their effectiveness, thereby greatly limiting the number of MSC that can be generated from a single donor.

One solution to this problem is the use of MSC derived from induced pluripotent stem cells (iPSC). iPSC can be generated from a number of different adult tissues and differentiated into MSC, which are referred to herein as "iMSC". Several of the advantages associated with the use of iMSC include the fact they can be propagated indefinitely, that they regain the functionality of young MSC even if derived from older individuals, and that they can serve as a single source of cells for treatment of multiple patients.

Therefore, iMSC lines were developed from both mouse and dog iPSC and evaluated their ability to exhibit bacterial killing activity in vitro. However, the previously noted unpredictability of MSC antibacterial activity made it impossible to predict the antibacterial activity of iMSC. Moreover, iMSC were found to express a very different surface phenotype from conventional BM-MSC or Ad-MSC.

Figure 25:
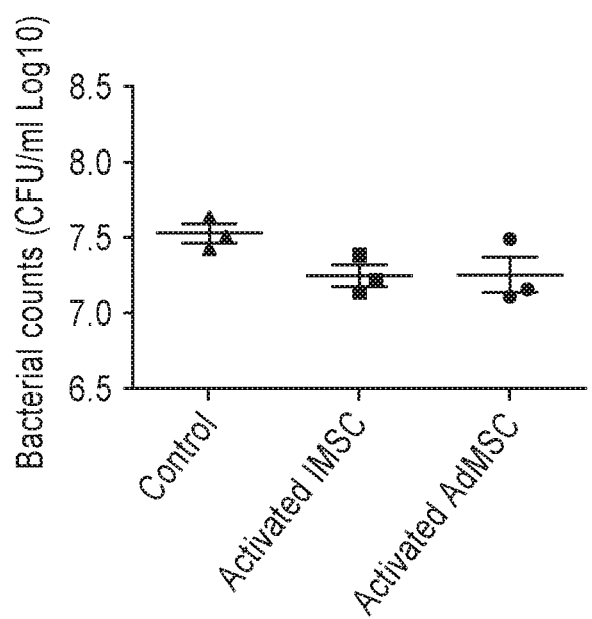
FIG. 25 is a graph showing that MSCs derived from induced pluripotent stem cells (iPSC) also exert antimicrobial activity.

However, it was found that activated iMSC from mice were equivalent to mouse Ad-MSC in terms of their ability to exhibit killing of *Staphylococcus* in vitro. (See FIG. 25).

Similar results in terms of antimicrobial activity were also obtained with canine iMSC compared to canine Ad-MSC.

Thus, iMSC are another source of MSC that can be used for treatment of drug resistant, chronic bacterial infections. Moreover, subpopulations of iMSC may potentially be further selected in vitro from iMSC cell lines for even greater antimicrobial activity before use in clinical patients, therefore making iMSC even more effective than conventional BM-MSC or Ad-MSC.

Activation of MSCs MSCs have been shown to exert an antimicrobial effect against bacteria though the secretion of antimicrobial peptides. (See Krasnodembskaya et al., Stem Cells 28(12):2229-2238 (2010), which is herein incorporated by reference). MSC have also been shown to secrete antimicrobial factors spontaneously in culture. (See FIG. 9). For example, murine, dog, and human MSCs all produce intracellular Cramp, an important antimicrobial peptide for killing both Gram-negative and Gram-positive bacteria. (See FIGS. 14 and 15).

Activation of MSCs using Toll-like receptor (TLR) ligands has been shown to enhance this antimicrobial effect. (See Johnson et al, The Journal of Immunology 190(1): Supplement 180.11 (2013), which is herein incorporated by reference; see also Zhao et al., Stem Cells 32(2):521-33 (2014)). However, in the Johnson reference, the antimicrobial activity was only demonstrated in vitro, and only against a fully antibiotic susceptible strain of *Staphylococcus aureus*. Moreover, in Johnson et al, it was found that activation of MSC in vitro did not in fact increase their antibacterial activity, as assessed by in vitro bacterial killing assays. Thus, it would be impossible to predict that activated MSC would be active in vivo against chronic wound infections, and in fact the Johnson at al publication would teach away from in vivo use of activated MSC. Moreover, it would also be impossible to predict MSC activity against strains of bacteria other than non-drug resistant *S. aureus*. It would also be impossible to predict activity against highly drug resistant strains of bacteria in vivo. Finally, it would also be impossible to predict MSC activity in mixed infections containing multiple different strains of highly drug resistant bacteria (e.g., infections containing MDR *E. coli* and *Pseudomonas aeruginosa*).

In contrast, as demonstrated herein, in vivo i.v. administration of activated MSCs reduced bacterial burden over time in wound tissue (see Example 2, infra), reduced viable bacterial at wound site (see Example 3, infra), and was shown to kill bacteria in vitro (see Example 9, infra). Moreover, i.v. administration of activated MSCs was also shown to be effective in vivo for the treatment of chronic wound infections. (See Examples 4-5, 7, 10, and 17-20, infra; see also FIGS. 18-24). Likewise, as shown in Table 1, infra, activated MSCs were effective against highly drug resistant strains of bacteria in vivo and were also simultaneously effective against multiple different strains of highly drug resistant bacteria.

In addition, it would be even more difficult to predict activity of MSC against highly drug resistant infections, for example, in patients with diabetes mellitus, who are known to possess significant immune deficiencies that limit their ability to control chronic bacterial infections. Without wishing to be bound by a particular theory, evidence suggests that the activated MSCs are acting through immune mediated mechanisms which would be expected to be limited in tissues with decreased vascularization, such as in diabetic wounds. (See FIGS. 11-13, 16). However, strong and unexpected activity of activated canine MSC in a dog with diabetes mellitus and a chronic (6 months) post-operative infection of the stifle which had not responded to repeated rounds of antibiotic therapy has been demonstrated. Following a single i.v. administration of MSC (see FIG. 22) the wound had partially healed and most importantly, the wound cultures became negative for the first time in months.

In addition, as described herein, activation of MSCs using one or more TLR3, TLR9, TLR4, and/or NOD receptor agonists enhances the antimicrobial effect of these cells. Examples of suitable TLR activating agents include, but are not limited to polyadenylic-polyuridylic acid (poly(A:U)), polyinosine-polycytidylic acid (poly(I:C) or pIC), CpG oligodeoxynucleotides (CpG ODNs), inhibitory oligodeoxynucleotides (ODNs), bacterial DNA, plasmid DNA, synthetic double stranded DNA or single stranded RNA, bacterial lipopolysaccharides (LPS), monophosphoryl lipid A (MPLA), and/or TLR7/8 ligands (e.g., imiquimod). In addition, MSC activation could also be achieved using NOD ligands, including peptidoglycans, uric acid, high concentrations of potassium, single stranded RNA, and other NOD ligands.

MSC activation can occur by in vitro or ex vivo incubation of the MSCs with an effective amount of the activating agent. For example, the MSCs can be incubated with the activating agent (i.e., pIC)) for 1, 2, 3, 4, 5, 6, 7, 8, 9, 10 or more hours. While determination of the appropriate concentration of the activating agent is within the routine level of skill in the art, concentrations of 1, 2, 3, 4, 5, 6, 7, 8, 9, 10, or more µg/ml are contemplated. In one embodiment, MSCs are activated by in vitro incubation with 10 µg/ml pIC for two hours.

Figure 26:
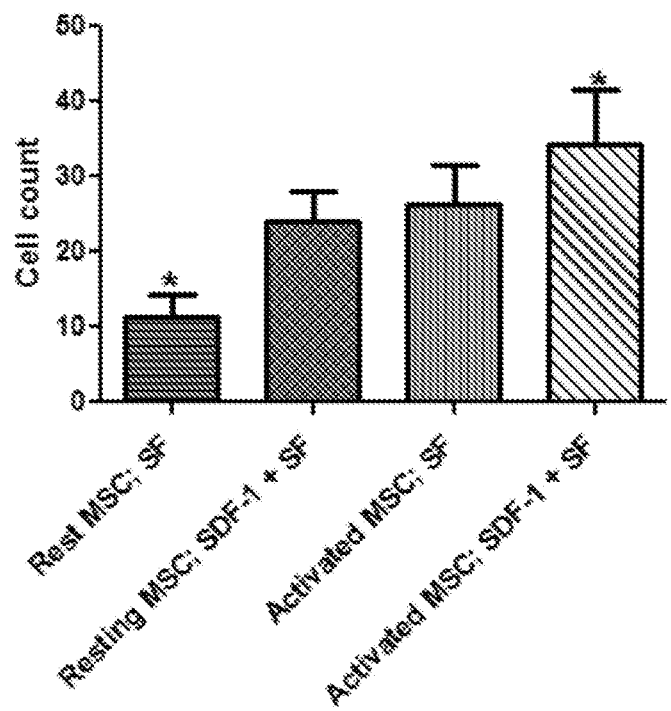
FIG. 26 is a graph showing that activation of MSC increases their migration.

Activation of MSC also increases their migration. For example, the ability of MSC to migrate in response to a chemokine gradient was evaluated using Boyden chambers that contained SDF-1 (stem cell derived factor-1, a chemokine for MSC) in the bottom chamber and MSC in the top chamber. Migration of MSC that were activated with pIC was found to be significantly greater than for non-activated MSC. (See FIG. 26). This increased migration of activated MSC to sites of inflammation is important to their ability to find their way to infected wounds following i.v. injection, as infected wounds produce high levels of SDF-1.

In addition, activated MSC have superior immunological properties with respect to migration to the wound site and recruitment of host immune effector cells (i.e., neutrophils and monocytes) (see FIG. 16), and activated mesenchymal stem cells exhibit increased antimicrobial activity compared to mesenchymal stem cells that have not been activated.

A strong synergistic interaction exists between activated MSCs and antibiotics in terms of eradicating bacteria in chronically infected wounds.

Administration

An effective amount of activated MSCs or any of the compositions described herein can be administered to a subject via an oral, topical, intravenous (i.v.), intra-arterial, intraocular, intraperitoneal, intrathecal, intraventricular, intraurethral, intrastemal, intracranial, intramuscular, or subcutaneous route of administration.

Figure 4:
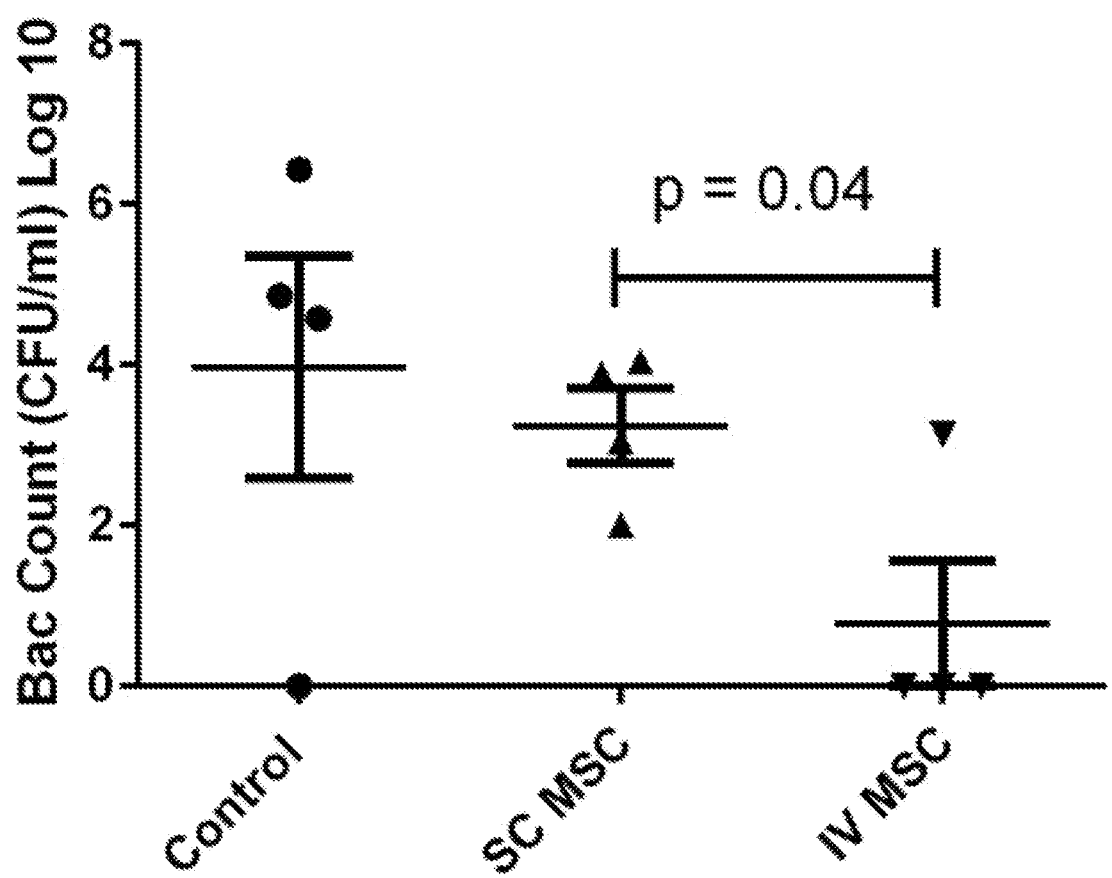
FIG. 4 is a graph showing a comparison of IV versus direct wound injection of activated MSC for treatment of chronic wound infections.

In one embodiment, the activated MSCs are administered intravenously. As shown in FIG. 4, intravenous administration of MSC is significantly more effective in reducing wound bacterial burden than SC administration. Moreover, while intravenously administered activated MSCs are initially trapped in the lungs, they are able to exit the lungs and migrate to sites of inflammation throughout the body. (See FIGS. 6 and 8).

Any suitable administration protocol known in the art can be used to administer the activated MSCs or the compositions described herein. The mesenchymal stem cells and/or compositions can be administered as a single dose or can be administered in multiple (i.e., 2, 3, 4, 5, 6, 7, 8, 9, 10, or more) doses.

Typically, patients will receive more than one (i.e., 2, 3, 4, 5, 6, 7, 9, 10, 11, 12, 13, 14, 15, 16, 17, 18, 19, 20, or more) doses of any of the compositions described herein and/or of the activated MSCs. When more than one dose is to be administered, the doses can be administered at regular or irregular intervals. By way of non-limiting example, the doses can be administered daily, weekly, biweekly, monthly, or bimonthly. For example the doses can be administered every 1, 2, 3, 4, 5, 6, or 7 days; every 1, 2, 3, 4, 5, 6, 7, 8, 9, 10, 11, or 12 weeks; and/or any combination thereof.

In one non-limiting example, three separate doses (i.e., three treatments) are administered over a 6 week period (i.e., every two weeks).

In some embodiments, between $1\times10^4$ and $1\times10^8$ cells per kg body weight can be administered with each dose. For example, about $2\times10^6$ cells per kg body weight may be administered slowly over a period of 15 minutes by i.v. catheter.

Determination of the appropriate dose (of activated mesenchymal stem cells per kg body weight), rate of administration, number of doses administered, and/or administration frequency for use in the treatment of a specific wound type is within the routine level of skill in the art.

Activated MSCs and the compositions described herein may additionally contain an effective amount of one or more antimicrobial agents, such as, a bactericidal antibiotic (e.g., penicillin derivatives (penams), cephalosporins (cephams), monobactams, carbapenems, vancomycin, daptomycin, fluoroquinolones, metronidazole, nitrofurantoin, co-trimoxazole, telithromycin, and/or aminoglycosidic antibiotics). Selection of the appropriate bactericidal antibiotic and effective dose thereof is within the routine level of skill in the art.

Additionally, in some embodiments, one or more bacteriostatic antibiotics can be administered (either alone or in combination with the one or more bactericidal antibiotics).

Systemic administration of activated MSCs was effective in eliminating bacteria associated with chronically infected wounds, when combined with antibiotic therapy.

Moreover, systemic administration of MSCs is also associated with a greater detail of wound healing in chronic infection models.

Compositions Provided herein are infusion-ready populations of MSCs that have been activated to enhance their antimicrobial effect along with one or more pharmaceutically or veterinarily acceptable carriers, diluents, excipients, or vehicles. These compositions enhance the healing of an infected or deep-seated wound in a mammal.

The terms "pharmaceutically acceptable" and "veterinarily acceptable" refer to a pharmaceutically- or veterinarily-acceptable material, composition, or vehicle, such as a liquid or solid filler, diluent, excipient, solvent, or encapsulating material. Each component must be "pharmaceutically acceptable" or "veterinarily acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. (See, Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004)).

In various embodiments, the population of activated MSCs may be allogeneic or autologous.

Figure 10:
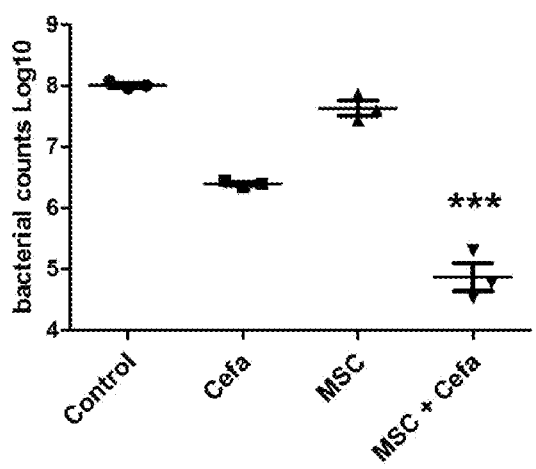
FIG. 10 is a graph demonstrating that MSC exhibit synergistic bacterial killing and reversal of high-level antibiotic resistance when combined with antibiotic therapy.

Any of the compositions described herein may additionally contain an effective amount of one or more antimicrobial agents, such as, a bactericidal antibiotic (alone or in combination with one or more bacteriostatic antibiotics). Exemplary bactericidal antibiotics include, but are not limited to penicillin derivatives (penams), cephalosporins (cephams), monobactams, carbapenems, vancomycin, daptomycin, fluoroquinolones, metronidazole, nitrofurantoin, co-trimoxazole, telithromycin, aminoglycosidic antibiotics, and any combinations thereof. Strong synergy has been observed when antibiotics and activated MSCs are combined. (See FIG. 10). Alternatively, a combination of activated MSC plus bacteriostatic antibiotics such as chloramphenicol, erythromycin, clindamycin, or tetracyclines may be considered.

A pharmaceutical composition of the disclosure is formulated to be compatible with its intended route of administration (i.e., parenteral, intravenous, intra-arterial, intradermal, subcutaneous, oral, inhalation, transdermal, topical, transmucosal, intraperitoneal or intra-pleural, and/or rectal administration). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions of cells. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In some embodiments, the MSC may also be pre-loaded with antibiotics prior to administration, in order to increase delivery of antibiotics directly to the site of the infected wound, with the MSC serving as the delivery mechanism. Particularly desirable antibiotics for this delivery method include antibiotics with high solubility in cells, including, but not limited to, floroquinolones, chloramphenicol, tetracyclines, and metronidazole. Preloading of MSCs with antibiotics can be accomplished by culturing MSCs with one or more antibiotics that are freely soluble across the cell membrane, prior to administration of the antibiotic-loaded MSC into the host.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

Kits, Medicaments and Articles of Manufacture

Activated MSCs either alone or in combination with one or more other therapeutic agents (e.g., one or more bactericidal antibiotics), may be used in the manufacture of the medicament, for example, a medicament for treating an infected or deep-seated wound.

Also provided are kits for treating chronically infected wounds containing any of the compositions described herein, optionally along with instructions for use.

Articles of manufacture are also provided, which include a vessel containing any of the compositions described herein and instructions for use for the treatment of an infected or deep-seated wound in a subject.

Any of the compositions described herein can be included in a container, pack, or dispenser together with instructions for administration Methods of Treatment Any of the compositions described herein can be used to treat a chronically infected wound with multi-drug resistant bacteria in a mammal. Likewise, an effective amount of activated MSC can also be used in the treatment of a chronically infected wound. For example, the compositions of MSCs can be used to treat highly drug-resistant infections.

Figure 24:
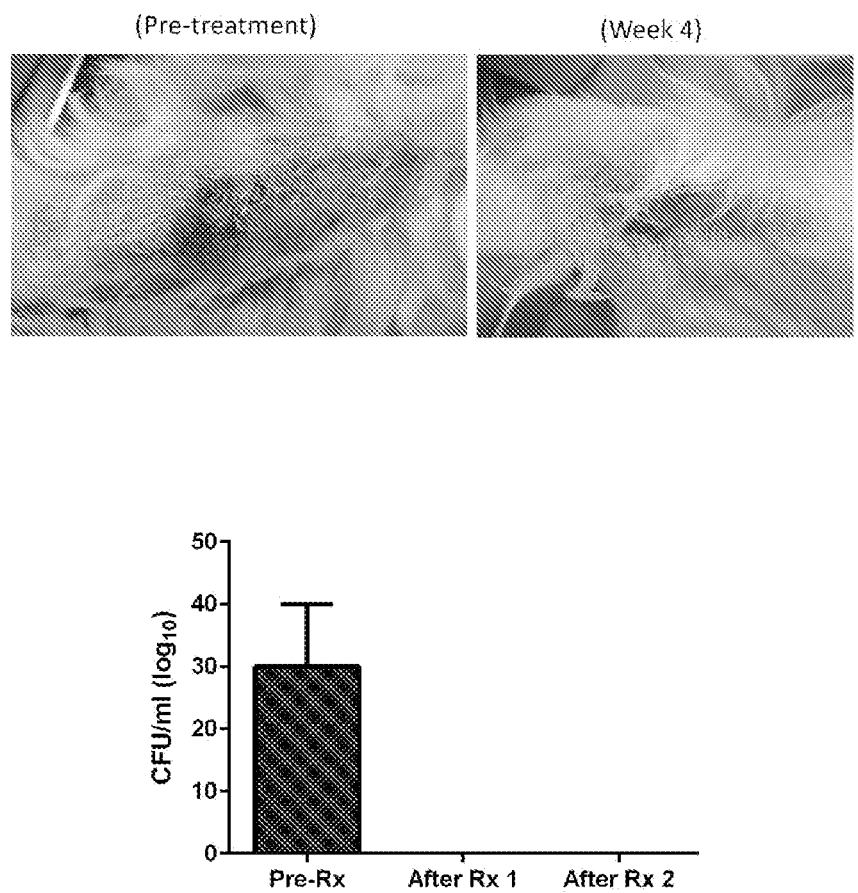
FIG. 24 is a series of before and after treatment photographs and culture results from a dog with diabetes mellitus and a chronically infected post-operative wound infection treated with a single i.v. administration of activated canine MSC, in conjunction with antibiotics.

Particular indications for the use of activated MSC for chronic wound infection treatment include treatment of diabetic patients having impaired immunity to infection (see FIG. 24). For example, the particular chronic wounds in these patients include infected ulcers (legs, feet, arms), infected implants, infected catheters, and osteomyelitis and other chronic infections of deep tissues. Other indications for activated MSC for wound infection treatment include the treatment of infections that contain multiple species or strains of MDR bacteria, including mixed infections with Gram-negative and Gram-positive infections, and mixed infections with different Gram-positive or Gram-negative bacteria (see FIGS. 17-19).

Methods are also provided where the compositions or activated mesenchymal stem cells are administered in conjunction (e.g., before, concurrently with, or subsequent to the administration of the compositions or the activated mesenchymal stem cells) with one or more antimicrobial agents such as a bactericidal antibiotic and/or a bacteriostatic antibiotic.

The specific combination of activated MSC or the composition described herein and bactericidal antibiotic therapy is required for efficient elimination of bacterial infection in deep tissues, and a strong synergy is observed when antibiotics and activated MSC are combined in vivo for treatment of deep bacterial infections. (See FIG. 10).

Figure 2:
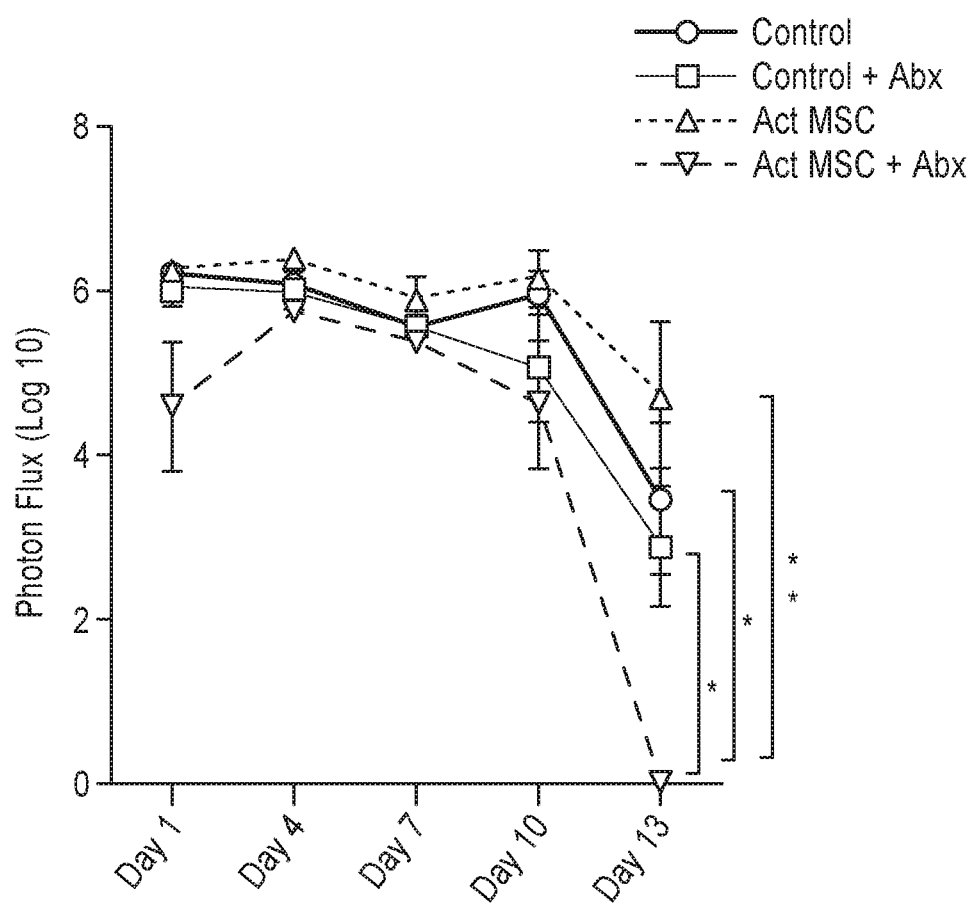
FIG. 2 is a graph demonstrating the reduction in bacterial burden over time in wound tissues following treatment with activated MSC and antibiotics in a mouse *S. aureus* wound infection model.

For example, the combination of activated MSC and oral antibiotics results in significant reductions in bacterial burden. (See FIG. 2). Likewise, this combination also significantly reduced the numbers of live bacteria at the site of the deep wound infection. (See FIG. 3).

Figure 27:
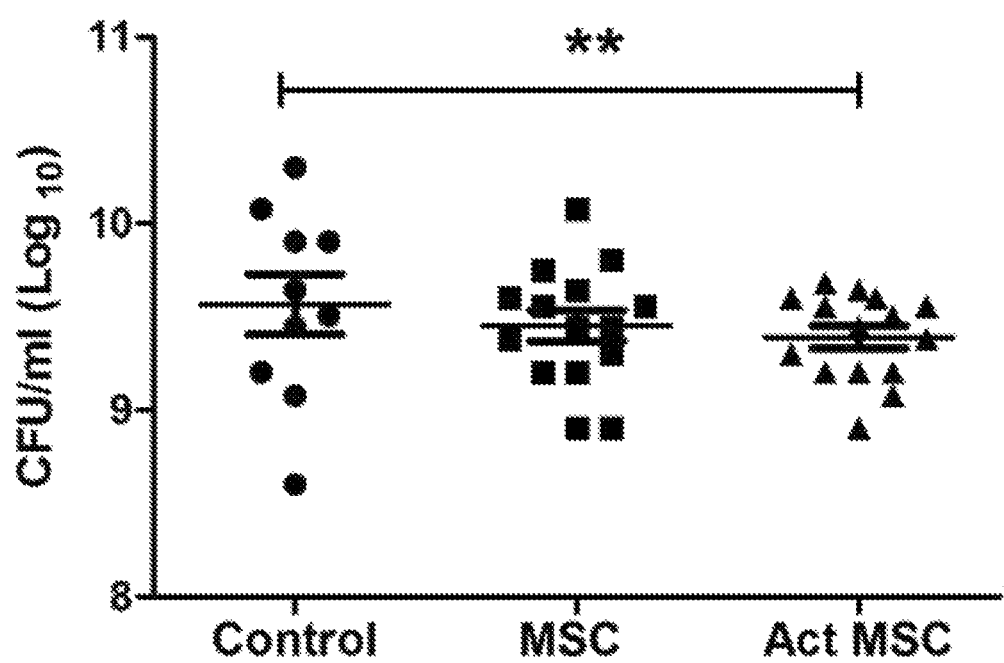
FIG. 27 is a graph showing that activated MSCs disrupt *S. aureus* biofilms.

Additionally, activated MSCs are also able to disrupt *S. aureus* biofilms. The ability of MSC to disrupt *S. aureus* biofilms was evaluated in vitro, using biofilm peg assays. Incubation of bacteria in the biofilm state with activated MSC revealed disruption of the biofilm, compared to biofilms alone or biofilms incubated with non-activated MSC. (See FIG. 27). In addition, an even greater disruption of biofilms was noted in biofilms of *Pseudomonas aeruginosa* bacteria. Because infections of implants associated with biofilm production are extremely difficult to eradicate with conventional antibiotic therapy, the combination treatments described herein (i.e., with activated MSCs and antibiotics) will be useful.

Administration of any of the compositions described herein or of the activated mesenchymal stem cells induces bacterial clearance and/or reduces bacterial burden in the infected wound, which, in turn, can enhance the healing of an infected wound.

Suitable compositions and/or activated mesenchymal stem cells (whether alone or in combination with one or more bactericidal and/or bacteriostatic antibiotics) can be administered at the time of or after the wound occurs. Additionally, MSCs may also be preloaded with one or more antibiotics.

It will be appreciated that administration of therapeutic entities in accordance with the disclosure will be administered with suitable carriers, excipients, and other agents that are incorporated into formulations to provide improved transfer, delivery, tolerance, and the like.

A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2): 1-60 (2000), Charman WN "Lipids, lipophilic drugs, and oral drug delivery-some emerging concepts." J Pharm Sci.89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The invention having been described, the following examples are offered by way of illustration and not limitation.

EXAMPLES

Example 1: Activated MSC Suppress Bacterial Wound Infection in Mouse Model of Deep Tissue *Staphylococcus aureus* Infection CD-1 mice (n=5 per group) were implanted with surgical mesh on which biofilms had been established with luciferase-expressing strain (Xen36) of *S. aureus*, which allowed the infection to be tracked using bioluminescence imaging. (See Walton et al., Comp Med. 64(1):25-33 (2014), which is herein incorporated by reference). The mesh was subsequently implanted subcutaneously to mimic a deep-seated surgical implant infection. On day 2 after implant placement, mice were randomly assigned to the following treatment groups: untreated controls; treatment with antibiotics (amoxicillin-clavulanic acid, continuous treatment in drinking water) only; treatment by i.v. administration of untreated MSC; treatment by i.v. administration of activated MSC; treatment by administration of untreated MSC plus antibiotics; and treatment with activated MSC plus antibiotics.

The activated MSC were administered i.v. at a dose of $5 \times 10^5$ cells per mouse for 4 treatments at 3-day intervals. The MSC were activated using a synthetic TLR3 ligand.

Mice were imaged by IVIS imaging every 2-3 days following mesh implantation to assess the effects of treatment on bacterial burden. Representative IVIS images of wounds in one mouse of each treatment group are depicted in FIG. 1.

The image demonstrates the disappearance of infection in the mice treated with antibiotics and activated MSC, whereas the infection persisted in the other groups of mice. The treatment effect was found to be dependent on 3 key factors: (1) activation of the MSC; (2) combining MSC administration with concurrent antibiotic therapy; and (3) i.v. administration of the MSC.

These findings demonstrate that local direct injection of the MSC into the wound did not control bacterial infection effectively and that administration of non-activated MSC with antibiotics also did not control infection. (See FIG. 3). Additionally, the administration of activated MSC alone also did not improve bacterial clearance when injected subcutaneously into infected wounds. Thus, the specific combination of activated MSC and bactericidal antibiotic therapy is required for efficient elimination of bacterial infection in deep tissues.

Example 2: Reduction in Bacterial Burden Over Time in Wound Tissues Following Treatment with Activated MSC and Antibiotics in Mouse *S. aureus* Wound Infection Model As described in Example 1, supra, CD-1 mice (n=5 per group) infected with *S. aureus* impregnated mesh were treated with activated MSC or with antibiotics, or both in combination. The numbers of *S. aureus* at the wound site were quantitated using IVIS imaging (image intensity directly proportional to number of viable bacteria), and the mean (+/−SEM) luciferase flux intensity was plotted over time of treatment.

Mice treated with activated MSC+oral antibiotics had significant reductions in bacterial burden at Day 13 of treatment compared to untreated control mice or mice treated with antibiotics (Abx) or activated MSC (Act MSC) alone. (See FIG. 2).

Example 3: Reduction of Viable Bacteria at Wound Infection Sites Following i.v. Delivery of Activated MSC Combined with Antibiotic Therapy CD-1 mice (n=5 per group) had chronic, deep *S. aureus* infections established using implanted, infected mesh, as described in Example 1, supra. The mice were then treated by 3 repeated i.v. injections at 3-day intervals of allogeneic adipose-derived mouse MSC. Treatment groups included untreated control animals (Ctrl), animals treated with oral amoxicllin-clavulanic acid alone (Abx), MSC alone (MSC), activated MSC alone (Act MSC), non-activated MSC plus antibiotics (MSC+Abx), or with activated MSC plus antibiotics (Act MSC+Abx), for 2 weeks. At the completion of 2 weeks of treatment, the animals were euthanized and wound tissues at the site of infection were collected and processed for quantitation of bacterial numbers of viable bacteria (colony forming units, or CFU) in the wound tissues using quantitative plating on LB agar quad plates.

Figure 3:
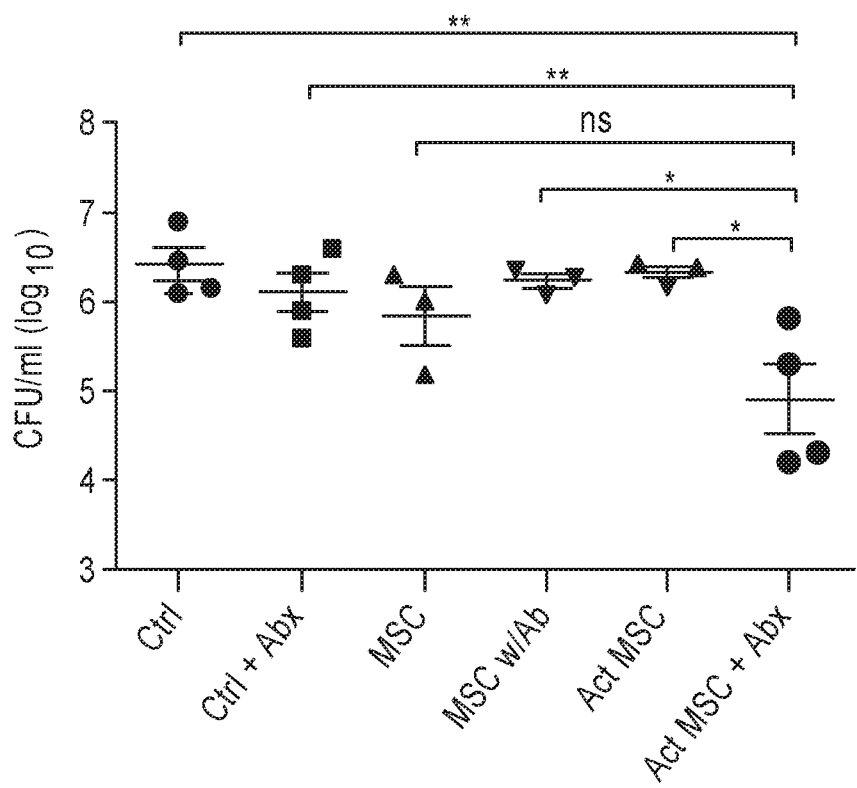
FIG. 3 is a graph demonstrating that treatment with activated MSC plus antibiotic reduces bacterial counts in wound tissues.

Mice treated with activated MSC plus antibiotics had significant reductions in their viable bacterial burdens at the wound site, compared to animals in the other treatment groups. (See FIG. 3). FIG. 3 also demonstrates that non-activated MSC were not effective in controlling infection when administered together with antibiotics. Likewise, only certain classes of antibiotics have been shown to be active for triggering the antibacterial effect with MSC.

Together, these findings indicate that activated MSC, when combined with bactericidal antibiotics, significantly reduce the numbers of live bacteria at sites of deep wound infection.

Example 4: Comparison of IV Versus Direct Wound Injection for Treatment of Chronic Wound Infections Mice with established *S. aureus* wound infections as described in Example 1, supra, were treated with oral antibiotics, plus activated MSC, administered by either direct injection in the perilesional tissues (SC), or by the i.v. route. The treatments were repeated 2 additional times at 3-day intervals. On day 14, the wound tissues were collected and the bacterial burden in the tissues determined by plating and colony counts.

The results shown in FIG. 4 demonstrate that intravenous administration of MSC was found to be significantly more effective in reducing wound bacterial burden than SC administration.

Figure 5:
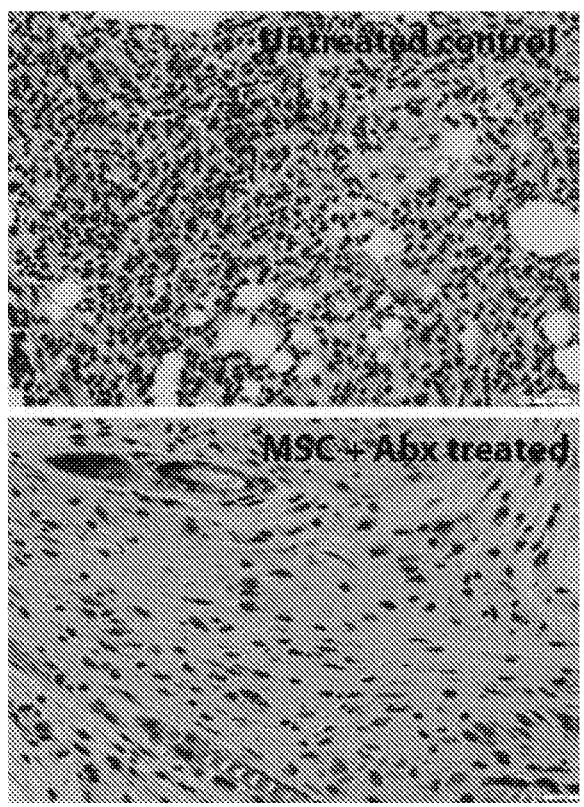
FIG. 5 is a series of photomicrographs showing the effects of activated MSC administration plus antibiotics on microscopic wound healing histology in a mouse chronic infection model.

Example 5: Effects of Activated MSC Administration Plus Antibiotics on Microscopic Wound Healing Features in Mouse Chronic Infection Model Mice with *S. aureus* infected mesh implants were treated as described in Example 1, supra. At the completion of the study (day 21), mice were euthanized and infected wound tissues were dissected to reveal the implant site. FIG. 5 depicts a representative photomicrograph (H & E stained tissue sections, 20×) of an untreated wound (top panel) and a wound treated with activated MSC plus antibiotics (bottom panel). In the treated wound, the inflammatory cell infiltrate is significantly reduced, and the inflammation is replaced with fibroblastic healing tissues. (See FIG. 5).

Figure 6:
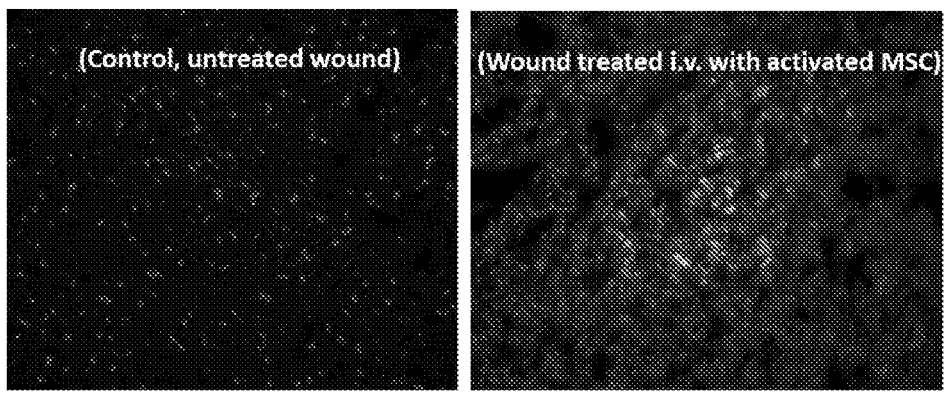
FIG. 6 is a series of photographs showing that activated MSC migrate efficiently to the wound infection site following intravenous administration.

Example 6: Activated MSC Migrate Efficiently to Wound Infection Site Following i.v. Administration Wound tissues from an infected control animal and from an infected animal injected i.v. with activated GFP-transgenic MSC ($1\times10^6$ MSC per mouse per injection) were evaluated by immunofluorescence imaging to detect MSC in wound tissues. As shown in FIG. 6, accumulation of large numbers of GFP+MSC at the wound site is evident in the image at right, which indicates that MSC efficiently migrate to the wound following i.v. administration.

These results indicate that even though most i.v. injected activated MSC are initially trapped in the lungs, the cells can efficiently exit the lungs afterwards and migrate to sites of inflammation throughout the body for days afterwards. This observation highlights one of the major advantages of the i.v. administration method, namely allowing the MSC to access infected sites anywhere in the body, and not just at cutaneous sites where they can be applied topically or by needle injection.

Example 7: Wound Healing Promoted by Systemic Treatment with Activated MSC

Figure 7:
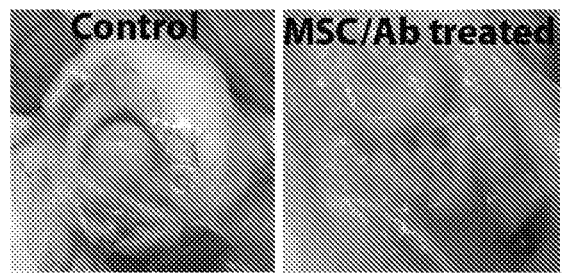
FIG. 7 is a series of photographs showing that wound healing is promoted by systemic treatment with activated MSC.

Mice with *S. aureus* infected mesh implants were treated as described in Example 1, supra. At the completion of the study (day 21), mice were euthanized and skin was dissected to reveal the implant site. FIG. 7 depicts a representative photograph of an untreated wound (control) and a wound treated with activated MSC plus antibiotics, with substantial healing evident in the MSC treated wound (right panel) compared to the untreated control wound (left panel). The untreated wound (left) is surrounded with a thick capsule of reactive tissue containing pus, while the MSC+antibiotics-treated wound (right) exhibits very little inflammation and no pus accumulation. The originally implanted surgical mesh material can also be visualized in the implant in the treated wound, whereas it is completely surrounded by pus in the untreated wound.

The wound healing effect was only observed in the group of mice treated with the activated MSC and antibiotics. Moreover, the results shown in FIG. 7 indicate that in addition to their ability to eradicate chronic deep-seated bacterial infection, the administration of activated MSC also contributes significantly to wound healing and reduction of inflammation and reactive scar tissue formation.

Example 8: Migration of DiR-Labeled MSC to Infected Wound Sites Following i.v. Administration In mice with *S. aureus* infected wounds (see Example 1, supra for details), activated or non-activated MSC were labeled with the infrared dye DiR (DiIC18(7) (1,1'-Dioctadecyl-3,3,3',3'-tetramethylindotricarbocyanine iodide)), and injected i.v. into live mice, which were then imaged in a bioluminescent imager (IVIS) to detect the migration of injected MSC. By 48 h post-injection, DiR+ cells were apparent in the region of the infected wound (middle and right panels, boxed area).

Figure 8:
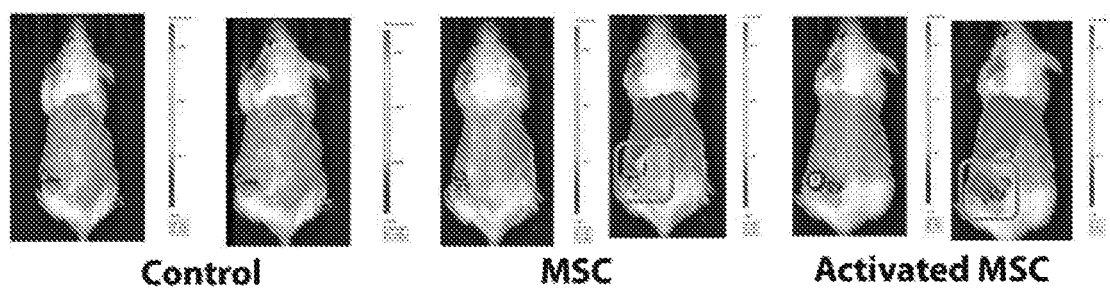
FIG. 8 is a series of photographs showing migration of DiR-labeled, activated MSC to infected wound sites following i.v. administration.

The results shown in FIG. 8 indicated that there were substantially more DiR+ cells in the region of the wound in mice injected with activated MSC (right panel) than in mice injected with non-activated MSC (middle panel). In control mice not injected with MSC (left panel), no infrared signal was detected. The region of wound infection with *S. aureus* is imaged as the blue-green region in each animal (left panel of each image). The large shaded regions in each mouse are the lungs, whereas the wound infiltrating cells are outlined in the boxed region.

Intravenous injected MSC trafficked efficiently to infected wounds, likely recruited in response to chemokines produced by inflamed tissues, and that activated MSC migrated more efficiently than non-activated cells. The fact that i.v. injected MSC progressively accumulated at the margin of infected wounds also indicated the importance of repeated MSC administrations for induction of the overall bacterial clearance effect.

Example 9: Bacterial Killing In Vitro by MSC

Figure 9:
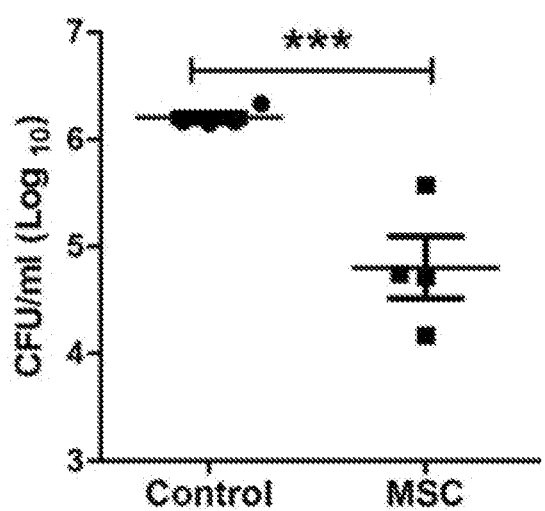
FIG. 9 is a graph demonstrating bacterial killing in vitro by MSC where *** denotes p<0.001 as assessed by non-parametric t-test.

The ability of MSC to kill *S. aureus* was assessed by co-culture of bacteria directly with MSC in vitro. MSC ($1\times10^5$ cells/well) were co-cultured with bacteria (10 bacteria per cell) in triplicate wells of 96-well plates for 4 h, then bacteria were collected from supernatants and CFU determined by manual counting. The results are shown in FIG. 9. Similar results were also observed when conditioned medium was collected from MSC cultures and incubated with bacteria.

These findings indicate that MSC secrete antimicrobial factors spontaneously in culture.

Example 10: MSC Exhibit Synergistic Bacterial Killing and Reversal of High-Level Antibiotic Resistance when Combined with Antibiotic Therapy Using a similar experimental design as described in Example 9, supra, highly antibiotic-resistant strains of bacteria were incubated with activated MSC alone, antibiotics alone (cefazolin (cefa)), or antibiotics+activated MSC in triplicate cultures and bacterial killing assessed 4 h later. When bacteria were incubated with very high doses of the antibiotic, little bacterial killing was observed. Likewise, significant bacterial killing was not observed with activated MSC alone.

However, administration of antibiotics combined with activated MSC demonstrated synergistic killing of bacteria as compared to either activated MSC or antibiotics alone. (See FIG. 10). Moreover, similar results were also observed with other antibiotics and with other bacterial strains. In addition, MSC from dogs and humans both also demonstrated this synergistic effect.

These findings support the rationale for combining MSC therapy with continued antibiotic therapy for treatment of chronic infections, even with antibiotics to which the bacteria are considered resistant, as they demonstrate that there is a unique and previously unappreciated anti-bacterial interaction between factors secreted by MSC and conventional bactericidal antibiotics such as cephalosporins and penicillins and aminoglycosides. In addition, this interaction accounts in part for the strong synergy observed when antibiotics and activated MSC are combined in vivo for treatment of deep bacterial infections.

Figure 11:
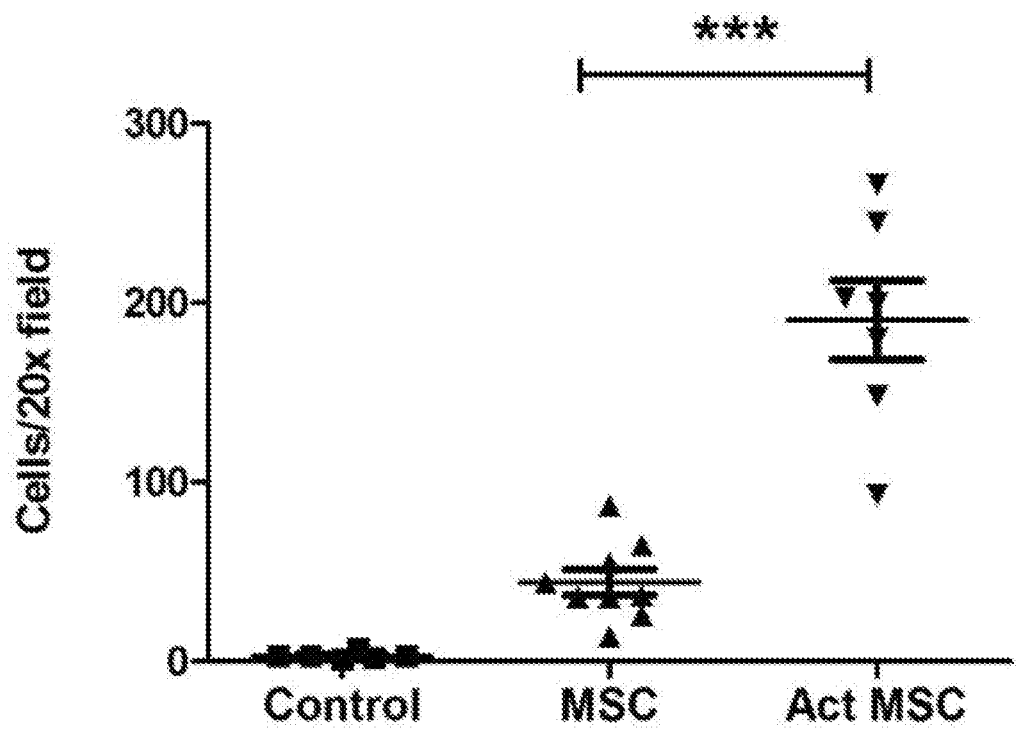
FIG. 11 is a graph demonstrating that chemokines produced by activated MSC stimulate monocyte migration in vitro.

Example 11: Chemokines Produced by Activated MSC Stimulate Monocyte Migration in Vitro Conditioned medium (CM) from MSC cultures was evaluated for the ability to stimulate monocyte migration, using migration assays (Boyden chambers) and blood from dogs. As shown in FIG. 11, incubation with CM from MSC stimulated enhanced monocyte migration, whereas incubation with CM from activated MSC (activated with pIC in vitro for 2 h) stimulated significantly greater monocyte migration.

These results indicate the activation of MSC with pIC can stimulate greater migration of monocytes to wound sites (see Example 12, infra).

Example 12: Systemic Administration of Activated MSC Triggers Monocyte Recruitment to Sites of Wound Infection Studies were done to investigate the impact of activated MSC on host immune responses, including monocyte, macrophage, and neutrophil responses. The numbers of monocytes migrating into wound tissues was determined by use of reporter mice whose inflammatory monocytes all expressed GFP. Wounds from *S. aureus* infected mice were immunostained for detection of inflammatory monocytes.

Figure 12:
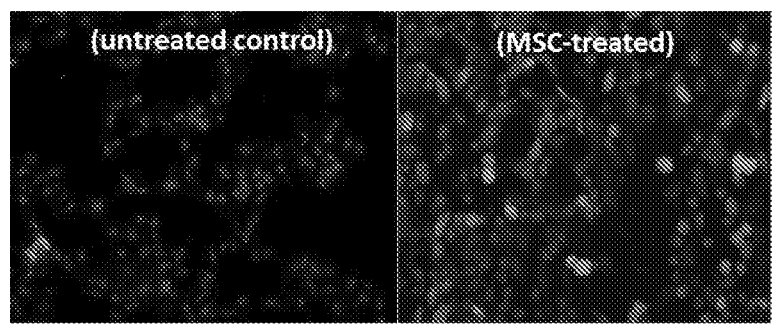
FIG. 12 is a series of photographs showing that systemic administration of activated MSCs triggers monocyte recruitment to sites of wound infection.

When mice with chronic *S. aureus* infected wounds (see Example 1, supra) were treated by i.v. administration of activated MSC, as shown in FIG. 12, there was a significant increase in the number of monocytes infiltrating the wounds (right panel), compared to untreated control animals (left panel). Wounds from untreated animals (left) or animals treated with antibiotics alone (not shown) contained a relatively sparse population of monocytes, whereas wounds from animals treated with activated MSC (right) contained a very dense population of monocytes recruited from the bloodstream. In addition, the numbers of monocytes migrating into wound tissues was significantly greater in animals treated with activated MSC than with non-activated MSC.

These findings demonstrate that MSC recruit host immune cells (monocytes) into tissues following i.v. administration, and also demonstrate that activation of MSC significantly enhances this monocyte recruitment effect. The monocyte-recruitment effect of activated MSC treatment is important because monocytes differentiate into macrophages in tissues and macrophages are key white blood cells for stimulating wound healing.

Figure 13:
FIG. 13 is a series of photographs showing that therapy with activated MSC stimulates the differentiation of wound-healing macrophages at the wound site and that treatment with activated MSC shifts macrophage polarization from M1 to M2 phenotype.

Example 13: Therapy with Activated MSC Stimulates the Differentiation of Wound-Healing Macrophages at the Wound Site As shown in FIG. 13, wound tissues from mice with chronic *S. aureus* wound infections were collected from untreated mice (left), mice treated with non-activated MSC (middle panel), and mice treated with activated MSC (right panel), and tissues from infected wounds were collected at 2 weeks and processed for detection of inducible nitric oxide expressing M1 macrophages (iNOS expression) and for detection of M2 macrophages (arginase expression). Mice treated with activated MSC (but not with un-activated MSC) had wounds that contained significantly more M2 than M1 macrophages, whereas just the opposite was observed in untreated animals or animals treated with un-activated MSC.

Because M2 macrophages are essential for wound healing, the increase in the number of M2 macrophages may help explain why wound healing is accelerated in animals treated with activated MSC. (See Example 12, supra).

Example 14: MSC Produce the Cathelicidin Antimicrobial Peptide LL-37

Figure 14:
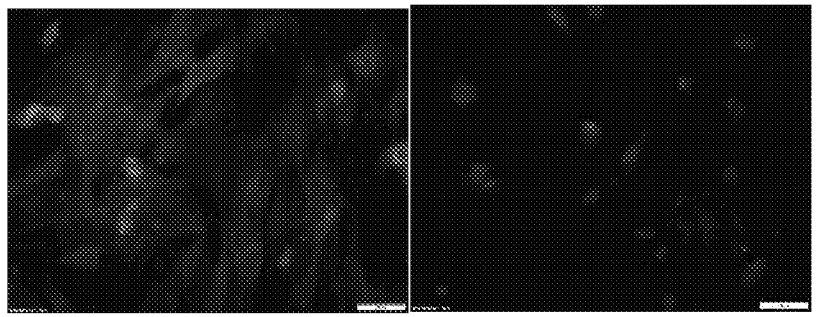
FIG. 14 is a series of photographs demonstrating that MSC produce the antimicrobial cathelicidin peptide LL-37.

As shown in FIG. 14, mouse MSC were immunostained for detection of intracellular production of the antimicrobial peptide LL-37 (left panel) or with an irrelevant isotype control antibody (right panel). Abundant expression of LL-37 was observed in the MSC (left panel), while little staining by the control antibody was observed.

These results indicate that murine, dog, and human MSCs all produce intracellular LL-37, which is an important antimicrobial peptide for killing both Gram-negative and Gram-positive bacteria.

It is likely that the demonstrated synergistic killing observed when MSC are combined with cefazolin is due to the release of LL-37 by MSC which then acts synergistically with the antibiotic to effect increased bacterial killing.

Example 15: Bacterial Killing by MSC Dependent in Part on Production of the Cathelicidin LL-37

Figure 15:
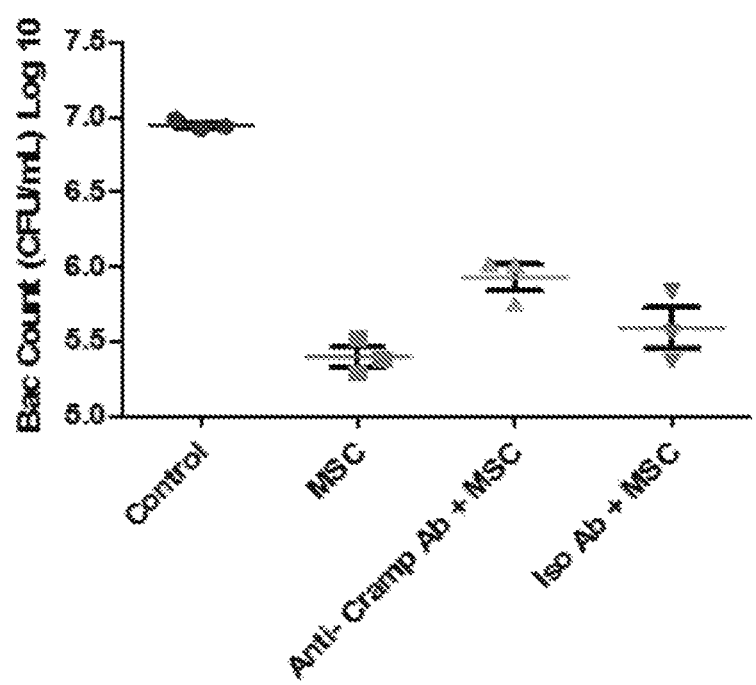
FIG. 15 is a graph demonstrating bacterial killing by MSC dependent in part on production of the cathelicidin LL-37.
Figure 16:
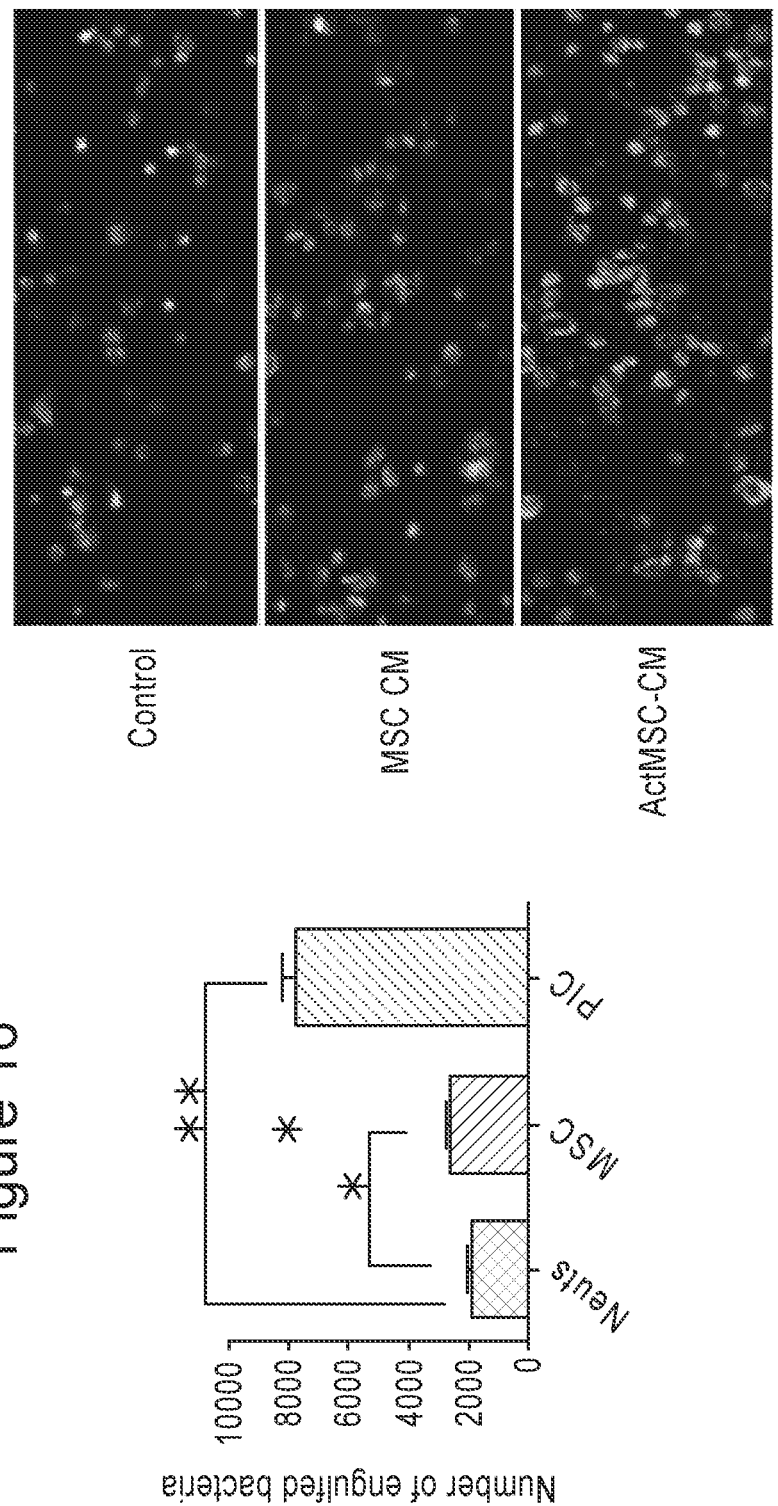
FIG. 16 demonstrates that factors produced by activated MSCs trigger increased bacterial phagocytosis by neutrophils.

As shown in FIG. 15, MSC were co-cultured with bacteria and the effects of LL-37 neutralization assessed. Bacterial killing activity by MSC was assessed in control MSC, in MSC that were also treated with an antibody that neutralized LL-37, and in MSC treated with an irrelevant antibody. Addition of the anti-Cramp antibody significantly reduced bacterial killing activity of MSC, indicating that MSC killing is mediated in part by secretion of the antimicrobial peptide LL-37.

Example 16: Factors Produced by Activated MSC Trigger Increased Bacterial Phagocytosis by Neutrophils Studies were performed to investigate the impact of activated MSC on host immune responses, including monocyte, macrophage, and neutrophil responses. Neutrophils were incubated with conditioned medium (CM) from MSC for 2 h, then washed and incubated with *Staphylococcus aureus* bacteria for 2 h. Extracellular bacteria were eliminated by antibiotic treatment, then bacteria were localized by immunostaining with an anti-*S. aureus* antibody. Neutrophils were localized by immunostaining for CD11b expression. Incubation with MSC CM significantly increased bacterial uptake, as noted in the bottom panel of FIG. 16. Neutrophils incubated with supernatants from activated MSC became significantly more phagocytic (right bottom panel and left panel) than control neutrophils (right top panel) or neutrophils incubated factors from un-activated MSC (right middle panel).

These results indicate one mechanism by which MSC may interact with the host immune system to enhance bacterial clearance. Moreover, activated MSC exert strong effects on the host innate immune system that can contribute to control of deep-seated bacterial infections.

Example 17: Intravenous Administration of Activated MSC Triggers Elimination of Multiple Strains of Drug-Resistant Bacteria in Infected Foot Wound in Dog with Infected Traumatic Foot Injury Clinical studies were conducted in pet dogs with naturally-occurring wounds and wound infections to evaluate the effectiveness of activated MSC and antibiotic therapy. A dog with a severely traumatized and infected foot wound (see FIGS. 18 and 19) was enrolled in a study evaluating the effectiveness of activated MSC therapy for wound infection control. The foot wound in this particular animal was infected with two highly antibiotic resistant bacterial isolates (*E. coli* and *Pseudomonas aeruginosa*) and had been treated without success for 2 weeks prior to entry into the study.

Figure 17:
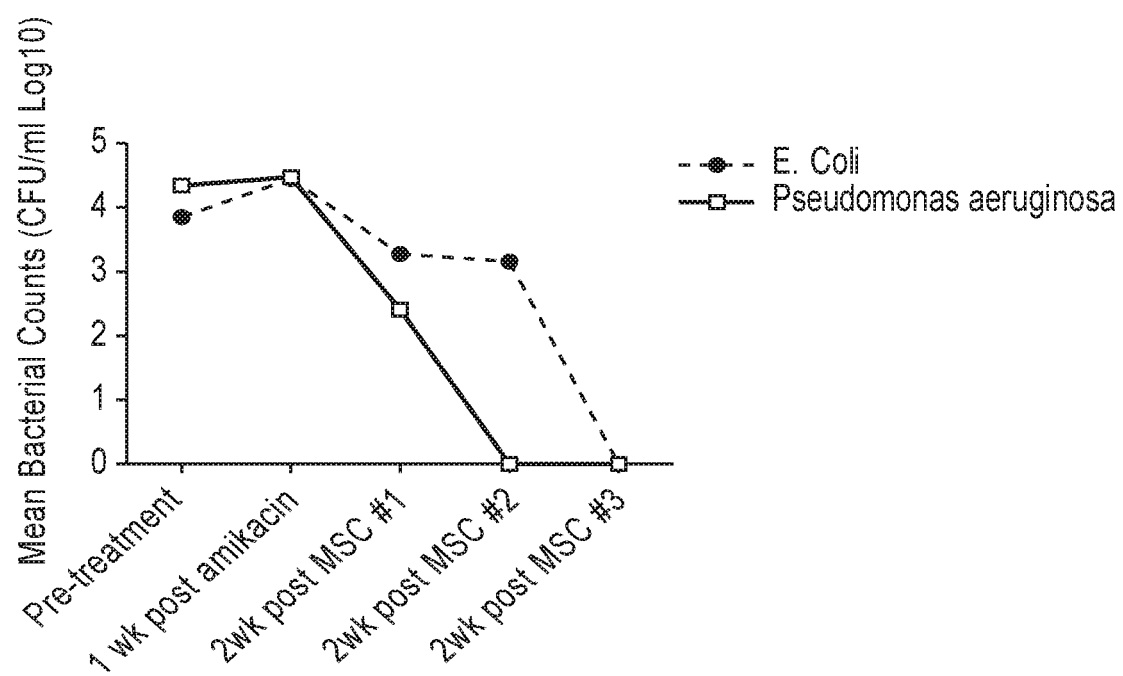
FIG. 17 is a graph demonstrating that intravenous administration of activated MSC triggers elimination of multiple strains of drug-resistant bacterial in infected foot wounds in dogs with infected traumatic foot injury.

The paw wound was treated with 3 i.v. infusions ($2\times10^6$ activated allogeneic MSC per kg body weight infused over a 15 minute period, at two week intervals) of activated, allogeneic canine MSC and the bacterial counts in the infected wound were determined by serial quantitative cultures taken over time during treatment (see FIG. 17). The dog also remained on the original daily antibiotic to which the bacteria were resistant to avoid confounding the study interpretation.

Prior to MSC treatment (but while still on antibiotic treatment), bacterial counts remained high. At week 2 (after the first MSC treatment), the numbers of both MDR *E. coli* and MDR *Pseudomonas* had decreased substantially, and the numbers continued to decline to undetectable levels by the completion of the 3rd MSC infusion (week 8).

Figure 18:
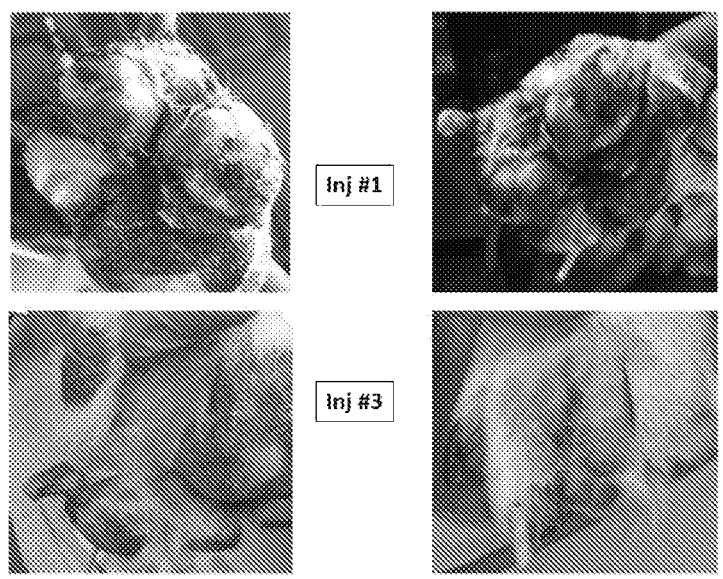
FIG. 18 is a series of photographs showing that systemic administration of activated MSC stimulates wound healing in dogs with infected traumatic foot injury.
Figure 19:
FIG. 19 shows the effects of activated canine allogeneic adipose-derived MSC on a non-healing, infect paw wound in a dog.
Figure 20:
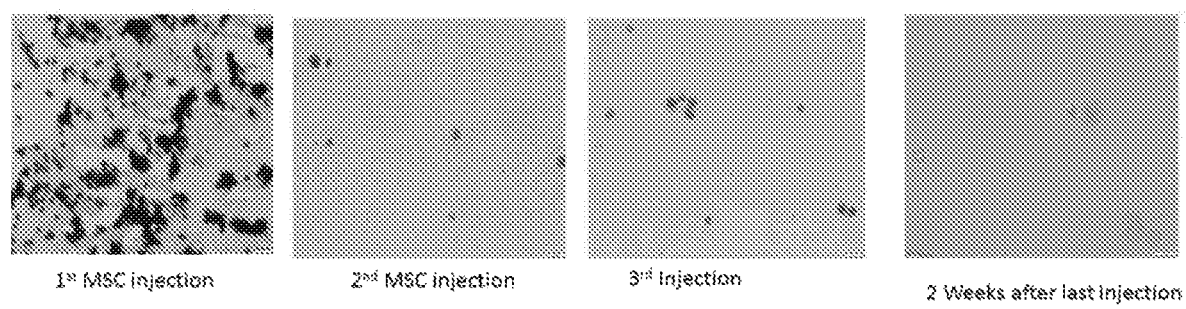
FIG. 20 is a series of photographs showing the resolution of chronic post-operative joint infection in a dog infected with MRSA by treatment with activated MSC.
Figure 21:
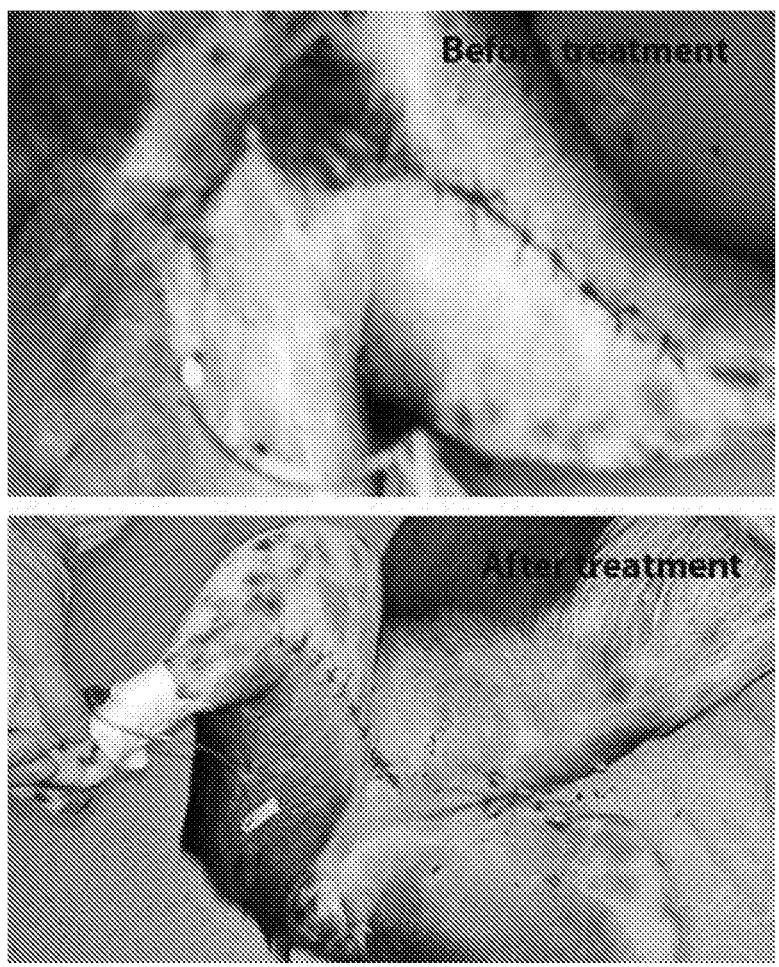
FIG. 21 is a series of photographs demonstrating wound healing in a dog with cutaneous infection with MDR *Enterococcus*.
Figure 22:
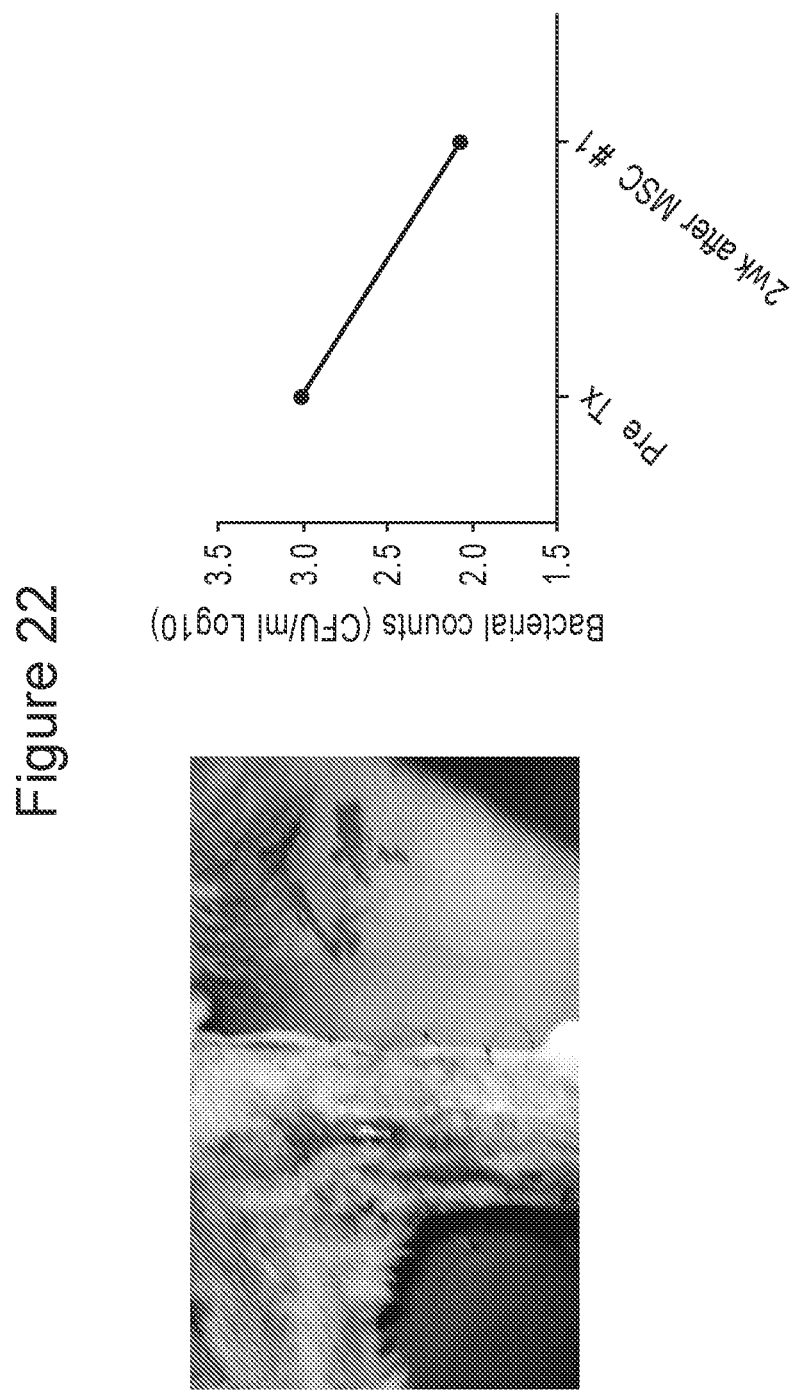
FIG. 22 shows treatment of osteomyelitis and bone plate infection in a dog with activated MSC and antibiotic therapy.

The infected paw wound described was also monitored photographically for wound healing, and the results are shown in FIGS. 18 and 19. At the time of the initial activated MSC injection (FIG. 18, Inj #1, top panels), the paw wound was very inflamed and painful and not healing. By the time of the third MSC injection (FIG. 18, bottom panels), the paw wounds had undergone significant healing and were no longer painful to the dog. Similarly, FIG. 19 shows that the wound was substantially healed at 4 weeks after 2 MSC treatments (right panel), compared to pre-treatment healing parameters.

Similar results regarding control of drug-resistant bacterial infections by i.v. administration of activated MSC combined with antibiotics were obtained in 4 additional dogs with chronic wound infections treated with activated MSC and antibiotics. These included two dogs with months long post-operative infections in their knee joints (see FIG. 20), a dog with chronically infected pacemaker leads, and a dog with chronically infected bone plate (see FIG. 21). In all 4 cases, after i.v. administration of the activated, allogeneic canine MSCs began, bacterial counts were significantly reduced or eliminated, and the wounds underwent substantial healing.

A summary of data obtained for dogs with MDR infections treated with activated MSC is provided in Table 1 below. Clinical data from 7 dogs with MDR wound infections in a variety of different sites that were refractory to conventional antibiotic treatment and enrolled and treated in a clinical trial evaluating the effectiveness of therapy with activated canine MSC for antimicrobial treatment. All dogs were evaluated for bacteriological and microbiological evidence of healing at 6 weeks.

TABLE 1

| Patient | Infection Site | Organism(s) | Bacteriologic response at 6 weeks | Wound healing at 6 weeks |
|---|---|---|---|---|
| 2 yr Lab | Left front paw-soft tissue injury | *Pseudomonas aeruginosa, E. coli* | Eliminated | Completely healed |
| 4 yr Pit Bull | R stifle joint - 6 months post op ACL repair | MRSP | Eliminated | Gait significantly improved |
| 9 yr Lab | R stifle joint - 1 year post op ACL | MRSP | Eliminated | Gait significantly improved |

TABLE 1-continued

| Patient | Infection Site | Organism(s) | Bacteriologic response at 6 weeks | Wound healing at 6 weeks |
|---|---|---|---|---|
| | repair | | | |
| 10 yr Corgi | Draining tract neck; infected pacemaker lead | MRSP - two strains | Unchanged | Improved - small draining tract remnant |
| 3 yr Leonberger | Left hind leg - infected bone plate with exposed bone | MRSP, E. coli, Corynebacterium, Kliebsiella | Eliminated all but MRSP | Improved - some bone tissue and plate still exposed |
| 10 yr Mastiff | Generalized moist dermatitis | MRSP | Eliminated | Improved |
| 8 yr Miniature Pinscher | Draining tract, left stifle | MRSP | Eliminated | Completely healed |

Taken together, all of these findings illustrate that the activated MSC product can be obtained from unrelated donor animals (i.e., allogeneic cells) and still be active. Moreover, a dose of activated MSC that is realistic for human clinical usage can be effective in eradicating complex mixtures of highly drug resistant organisms in realistic wound infection models.

These results also demonstrate the strong healing activity of activated MSC, when they are administered systemically in animals with highly drug resistant bacterial infections. Additionally, because the results were obtained in a spontaneous, realistic animal model of human bacterial infection, these findings can be readily applied to the treatment of human or animal infections.

Example 18: Treatment of Chronic Joint Infection with Activated MSC Plus Antibiotics in Dog with Post-Surgical Infection A dog with a non-resolving, post-operative stifle infection of 1 year duration that had persisted through 2 additional surgeries and multiple courses of antibiotic therapy was enrolled in a study to evaluate the antimicrobial properties of activated canine MSC. During the study, the dog remained on the original (ineffective) antibiotic regime, while receiving 3 infusions of activated allogeneic canine adipose-derived MSC at 2-week intervals. The response to treatment was monitored by serial evaluation of joint fluid cytology, obtained by arthrocentesis. (See FIG. 20).

The initial joint fluid contained large numbers of inflammatory cells, which rapidly began to disappear during treatment, until the joint fluid was normal by week 8 of the study. In addition, the dog improved dramatically clinically and could begin to use the limb again normally by week 8. The dog remains clinically normal 1 year later.

Therefore, these findings indicate that activated MSC therapy combined with antibiotics can be effective against even in deep infections in sites such as the knee joint, and in a spontaneous disease model that closely resembles human post-op infections.

Example 19: Wound Healing in Dog with Cutaneous Infection with MDR Enterococcus

A dog developed infection with MDR Enterococcus sp following surgical repair of a traumatic skin wound, and the infection was not responsive to antibiotic therapy. Thus, the dog was enrolled in a clinical trial to evaluate the ability of activated canine MSC to resolve the wound infection and stimulate wound healing. During the study, the dog received a series of 3 i.v. infusions of activated canine allogeneic adipose-derived MSC over an 8-week period. At the completion of the study, the wound was substantially healed (see FIG. 21, left panel), compared to pre-treatment, and Enterococcus could no longer be cultured from the wound (see FIG. 21, right panel).

Example 20: Treatment of Osteomyelitis and Bone Plate Infection in a Dog with Activated MSC and Antibiotic Therapy A dog developed chronic and antibiotic resistant infection following a fracture repair with a bone plate. (See FIG. 22, left panel). The dog was then treated with 3 infusions of activated allogeneic canine MSC, at 2-week intervals, while remaining on the original antibiotic. Quantitative cultures were done from a dog with a bone plate infected with multiple different species of MDR bacteria, before treatment and 2 weeks after the first i.v. infusion of activated MSC. After one MSC injection, the numbers of bacteria isolated from the infected wound decreased significantly at week 4 of treatment. (See FIG. 22, right panel).

These findings indicate that systemic administration of activated MSC can also be effective against implant infections such as bone plates, which are notoriously difficult to treat with antibiotics alone. Despite this known difficulty, the combination of activated MSC and antibiotic therapy resulted in a marked drop in bacterial count within only 2 weeks of MSC administration.

Example 21: Healing and Clearance of Chronic MDR Wound Infection in a Cat Following Systemic Therapy with Activated Feline Mesenchymal Stem Cells A cat spontaneously developed vasculitis and subsequent loss of a large portion of the skin over the neck and back. The wound was managed with frequent bandage changes, but subsequently became infected with several different bacterial isolates. The cat was placed on an antibiotic (enrofloxacin), but the wound continued to be infected and grossly necrotic and the cat became systemically ill.

At the time of enrollment in the antimicrobial stem cell study, the wound cultures grew highly drug-resistant *Staphylococcus intermedius*. The cat next received a series of i.v. infusions of activated feline allogeneic MSC, administered at a dose of $2 \times 10^6$ cells per kg body weight, administered every 2 weeks for 3 treatments. During the treatment trial, the cat continued to only be treated with enrofloxacin, to which the Staph isolate was resistant.

Figure 23:
FIG. 23 is a series of photographs demonstrating healing of a large chronically infected wound in a cat following a series of treatments with iv-administered, activated feline MSC in conjunction with antibiotics.
Figure 23:
Figure 23:
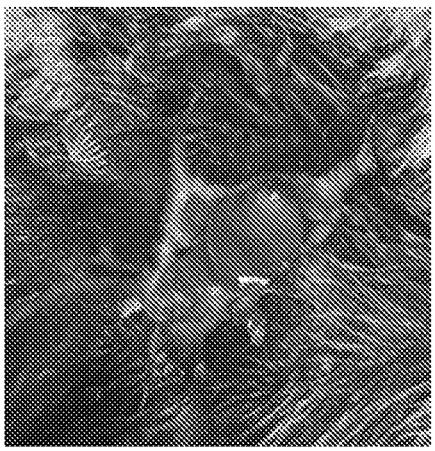
Figure 23:
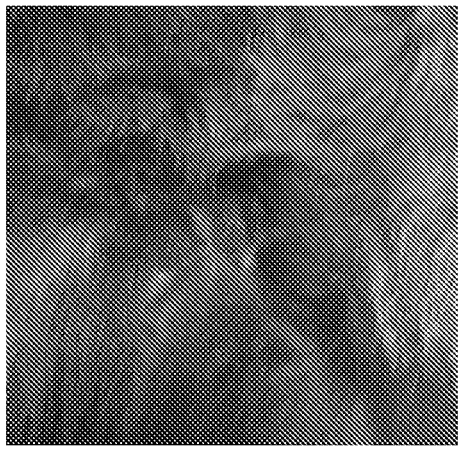

The results are shown in FIG. 23. Within 24 h of receiving the first stem cell treatment, the cat was noticeably clinically improved. At recheck at 3 weeks, the wound was noticeably smaller and less discharge was noted, though *Staphylococcus* was isolated from wound fluid. At week 5, the wound was smaller still, and the wound tissues looked much healthier, and the wound cultures were negative. At 7 weeks, the wound was almost completely healed and the wound cultures were negative. The cat received no further treatment and the wound was considered resolved.

Example 22: Treatment of Chronic Wound Infection with Multiple Strains of MDR Bacteria in a Dog with Diabetes Mellitus FIG. 24 shows wound healing and resolution of infection in a dog with diabetes mellitus and a chronically infected post-operative wound. A dog with long-standing diabetes mellitus developed a post-operative wound infection of the knee joint, which remained refractory to conventional antibiotic therapy over a 3-month period following treatment with several different antibiotics.

At the time of entry into the stem cell trial, the wound was red and inflamed and oozing purulent material. The dog was treated with a series of i.v. infusions of 2×106 cells per kg of activated allogeneic canine MSC, administered at 2-week intervals. Pre-treatment quantitative wound cultures revealed 2 different isolates of highly MRD *Staphylococcus epidermidis*.

Two weeks after the first MSC infusion, the wound appearance had improved and the owner reported the dog was less lame. In addition, wound cultures returned with no growth.

After the second MSC infusion, the wound appearance had markedly improved and wound cultures were again negative. The serous exudate noted on the wound at week 4 (see FIG. 24) was sterile and had been observed previously in other wounds during treatment with activated MSC, and typically resolves spontaneously.

Example 23: Treatment of Chronic Wound Infections Antibiotic-Loaded MSCs and Antibiotic Therapy MSC are expanded in culture in vitro, then are incubated with cell permeable antibiotics (e.g., quinolones, tetracyclines, metronidazole) for 1-2 hours and concurrently, previously, or subsequently activated with pIC. Activated and loaded MSCs are washed and collected prior to being infused i.v. as described supra. Treatments with antibiotic loaded cells would be repeated at 1-2 week intervals until wound resolution occurred.

Preferred patients for this approach (versus MSC not loaded with antibiotics) would include subjects with particularly drug resistant infections (e.g., highly drug resistant infections), patients with infections where antibiotics do not penetrate tissues well after oral or i.v. delivery; and patients with infections where it is desirable not to administer drugs orally or parenterally to avoid disrupting the normal bacterial flora (e.g., *C. difficile* susceptible patients).

EQUIVALENTS

The details of one or more embodiments of the invention are set forth in the accompanying description above. Although any methods and materials similar or equivalent to those described herein can be used in the practice or testing of the present invention, the preferred methods and materials are now described.

The foregoing description has been presented only for the purposes of illustration and is not intended to limit the invention to the precise form disclosed, but by the claims appended hereto.

What is claimed is:

1. A method of treating a non-healing infected or chronically infected tissue in a subject, the method comprising:
    a) obtaining activated mesenchymal stem cells (MSCs) comprising MSCs exposed to one or more activating agents for up to 10 hours or more comprising at least one Toll- like receptor 3 (TLR3) agonist of polyinosine-polycytidylic acid (pIC), polyadenylic-polyuridylic acid (poly(A:U), and UV-inactivated viral particles in an amount sufficient to obtain activated MSC having increased ability to migrate to the non-healing infected or chronically infected tissue relative to MSC that have not been exposed to the activating agent; and
    b) administering a pharmaceutical composition comprising the activated MSCs obtained in a) to the subject and treating the non-healing infected or chronically infected tissue in the subject.

2. The method of claim 1, wherein the chronically infected tissue comprises a chronic bacterial infection and the pharmaceutical composition induces bacterial clearance, reduces bacterial burden, or induces bacterial clearance, and reduces bacterial burden in the chronically infected tissue.

3. The method of claim 2, further comprising obtaining or harvesting the MSCs from bone marrow, adipose tissue, cord blood, umbilical cord tissue, placenta, tissue biopsies, dental biopsies, or blood of a mammal.

4. The method of claim 1, further comprising intravenously administering the composition to the subject.

5. The method of claim 1, further comprising obtaining or harvesting the MSCs from a biopsy comprising a skin biopsy or a dental biopsy.

6. The method of claim 1, wherein the one or more TLR3 agonist comprises pIC.

7. The method of claim 1, wherein the UV-inactivated viral particles are poxvirus particles.

8. The method of claim 1, wherein the one or more activating agent is synthetic pIC.

9. The method of 1, further comprising administering to the subject one or more antimicrobial agents, before, during or after administering the activated MSCs to the subject.

10. The method of claim 9, wherein the one or more antimicrobial agents is a bactericidal antibiotic.

11. The method of claim 10, wherein the bactericidal antibiotic is selected from the group consisting of penicillin derivatives (penams), cephalosporins (cephams), monobactams, carbapenems, vancomycin, daptomycin, fluoroquinolones, metronidazole, nitrofurantoin, co-trimoxazole, telithromycin, and aminoglycosidic antibiotics.

12. The method of claim 9, wherein the activated MSCs in combination with the one or more antibacterial agent act synergistically to treat the-non-healing infected or chronically infected tissue in the subject.

13. The method of claim 9, wherein the activated MSCs and the one or more antimicrobial agent are administered to the subject at the same time or sequentially by the same or different routes of administration.

14. The method of claim 1, wherein the MSC are mammalian MSCs.

15. The method of claim 1, wherein the MSCs are human MSCs.

16. The method of claim 1, wherein the activated MSCs enhance healing of the non-healing infix-led or chronically infected tissue in the subject.

17. The method of claim 1, wherein the chronically infected tissue comprises one or more of abrasions, deep-seeded or inaccessible wounds, diabetic ulcer, lacerations, contusions, concussions, stab wounds, skin cuts, surgical wounds, gunshot wounds or other trauma, ischemia/reperfusion injury, vascular disease, hums, sunburns, frostbite, chemical wounds, insect bites, animal bites, infected wound, stings and electrical wounds comprising a chronic infection.

18. The method of claim 1, wherein the activated MSCs are administered to the subject daily, biweekly, weekly, every other week, monthly, or every other month for a predetermined period of time or as determined by a health professional.

19. The method of claim 1, wherein the non-healing infected tissue comprises a non-healing infected tissue having mixed populations of bacteria.

20. The method of claim 1, wherein the non-healing infected tissue comprises a non-healing infected tissue comprising drug resistant bacteria.

21. The method of claim 1, wherein the administered MM SCC stimulate the recruitment of monocytes to the infected tissue.

22. The method of claim 21, wherein the monocytes differentiate into macrophages comprising M1 and M2 macrophages.

23. The method of claim 1, wherein the chronically infected tissue comprises at least one of a chronically infected tissue infected with at least one drug-resistant bacteria and a chronically infected tissue infected with two or more different bacterial species or strain.

24. The method of claim 1, wherein the chronically infected tissue comprises a mixture of more than one Gram-negative bacterial species or strains, more than one Gram-positive species or strains; or a mixture of Gram-negative and Gram-positive bacterial species or strains.

25. The method of claim 1, wherein the chronically infected tissue comprises a tissue within which there is an established chronic bacterial biofilm infection.

26. The method of claim 1, wherein the MSC are allogeneic, autologous, or xenogeneic mesenchymal stem cells (MSCs) and mesenchymal stem cells derived from induced pluripotent stem cells (iPSCs), iMSCs.

27. The method of claim 26, wherein the iPSC cells are derived from tissue biopsies or blood.

28. The method of claim 1, wherein the activated MSCs comprise activating the MSCs by exposing the MSCs or iMSCs to plc in vitro at about 10 g/ml.

29. The method of claim 26, wherein the effective amount of activated MSCs or iMSCs comprises about $1\times10^4$ to about $1\times10^8$ lift cells per kg body weight of the subject.

30. The method of claim 29, wherein the activated MSCs are administered by intravenous catheter, by direct injection into or around the infected tissue.

* * * * *